United States Patent
Macolly, Jr. et al.

(10) Patent No.: US 7,039,387 B2
(45) Date of Patent: May 2, 2006

(54) SYSTEMS, METHODS AND COMPUTER PROGRAM PRODUCTS FOR RESPONDING TO AMBER ALERTS

(75) Inventors: Henry Macolly, Jr., Marietta, GA (US); Frank P. May, Powder Springs, GA (US)

(73) Assignee: BellSouth Intellectual Property Corporation, Wilmington, DE (US)

( * ) Notice: Subject to any disclaimer, the term of this patent is extended or adjusted under 35 U.S.C. 154(b) by 203 days.

(21) Appl. No.: 10/702,845

(22) Filed: Nov. 6, 2003

(65) Prior Publication Data

US 2005/0101286 A1 May 12, 2005

(51) Int. Cl.
H04M 11/04 (2006.01)

(52) U.S. Cl. ............... 455/404.1; 455/404.2; 455/521; 340/539.13; 340/573.4; 342/357.09; 379/265.04; 379/266.01; 379/59; 379/57; 705/8; 705/13; 705/37; 705/51

(58) Field of Classification Search ............... 455/404, 455/404.1, 521; 340/539.1, 573.4; 342/357.09; 379/265.04, 266.01, 59, 57; 705/8, 13, 37, 705/51
See application file for complete search history.

(56) References Cited

U.S. PATENT DOCUMENTS

| | | | | |
|---|---|---|---|---|
| 5,563,931 A | * | 10/1996 | Bishop et al. | ............ 455/404.1 |
| 6,028,514 A | * | 2/2000 | Lemelson et al. | ..... 340/539.13 |
| 6,731,238 B1 | * | 5/2004 | Johnson | ................. 342/357.09 |
| 2003/0022684 A1 | * | 1/2003 | Seeger | ....................... 455/521 |
| 2003/0030561 A1 | * | 2/2003 | Yafuso et al. | ............ 340/573.4 |
| 2003/0109245 A1 | * | 6/2003 | McCalmont et al. | ....... 455/404 |
| 2003/0121036 A1 | | 6/2003 | Lock et al. | |
| 2003/0218535 A1 | | 11/2003 | Khoshbin | |
| 2004/0103158 A1 | | 5/2004 | Vella et al. | |
| 2004/0104808 A1 | | 6/2004 | Khoshbin | |
| 2004/0143391 A1 | | 7/2004 | King et al. | |
| 2005/0030977 A1 | | 2/2005 | Casey et al. | |

OTHER PUBLICATIONS

U.S. Appl. No. 10/388,335, filed Mar. 13, 2003, Dennis et al., *Systems, Methods and Computer Program Products for Communicating AMBER Alerts to a Mobile Workforce.*
*AMBER Plan—America's Missing: Broadcast Emergency Response*, http://www.missingkids.com/html/amberplan.html, 6 pages.

\* cited by examiner

Primary Examiner—William Trost
Assistant Examiner—Michael Vu
(74) Attorney, Agent, or Firm—Myers Bigel Sibley & Sajovec

(57) ABSTRACT

An AMBER alert gateway includes a central telephone number that is configured to receive telephone calls from individuals in response to potential sightings related to AMBER alerts. An interactive voice response system is configured to selectively direct telephone calls that are responsive to a selected AMBER alert to a selected authority who is responsible for the selected AMBER alert. Efficient processing of potential sightings thereby may be provided. Related systems, methods and computer program products also are disclosed.

16 Claims, 19 Drawing Sheets

TEST MESSAGE FOR AMBER ALERT FOR BELLSOUTH

WE HAVE JUST RECEIVED THIS IMPORTANT ANNOUNCEMENT REGARDING A MISSING CHILD IN OSCEOLA COUNTY. THE OSCEOLA SHERIFF" OFFICE AND THE FLORIDA DEPARTMENT OF LAW ENFORCEMENT ARE LOOKING FOR ELIZABETH MURRELL, A WHITE FEMALE, 12 YEARS OF AGE, 4 FOOT 11 INCHES TALL, WEIGHING 85 POUNDS WITH BROWN HAIR AND BROWN EYES AND HER SISTER AMANDA MURRELL, A WHITE FEMALE, 9 YEARS OF AGE, 4 FOOT 9 INCHES TALL, 75 POUNDS WITH BROWN HAIR AND BROWN EYES. BOTH CHILDREN WERE LAST SEEN AT THE TROPICAL PALMS CAMPGROUND AREA AT 2650 HOLIDAY TRAIL AND ARE BELIEVED TO BE IN EXTREME DANGER. ELIZABETH MURRELL WAS LAST SEEN WEARING A BURGUNDY JACKET AND BLUE JEANS. AMANDA MURRELL WAS LAST SEEN WEARING A BLUE GRAY WIND BREAKER AND UNKNOWN COLOR OF PANTS. IF YOU HAVE ANY INFORMATION ON THE WHEREABOUTS OF ELIZABETH AND AMANDA MURRELL PLEASE CONTACT THE OSCEOLA COUNTY SHERIFF'S OFFICE AT 407-348-2222 OR THE FDLE AT 1-888-356-4774 (1-888-FLMISSING).

SYSTEMS, METHODS AND COMPUTER PROGRAM PRODUCTS FOR RESPONDING TO AMBER ALERTS

FIELD OF THE INVENTION

This invention relates to communications systems, methods and computer program products, and more particularly to systems, methods and computer program products for communicating an urgent bulletin in child abduction cases.

BACKGROUND OF THE INVENTION

In the fall of 2001, the National Center for Missing and Exploited Children (NCMEC) launched the AMBER plan: America's Missing: Broadcast Emergency Response, across the United States. As is well known to those having skill in the art, the AMBER plan is a voluntary partnership between law enforcement agencies and broadcasters to activate an urgent bulletin, known as an AMBER alert, in the most serious child-abduction cases. Broadcasters use the Emergency Alert System (EAS), formerly called the Emergency Broadcast System, to air a description of the abducted child and a suspected abductor. The goal of the AMBER alert is to instantly galvanize the entire community to assist in the search for and safe return of the child. The AMBER plan was created in 1996 as a legacy to nine year old Amber Hagerman who was kidnapped and brutally murdered while riding her bicycle in Arlington, Tex. In some states, the AMBER alert is known by a different name such as Levi's Call in Georgia, named for a young boy who was abducted and brutally murdered in 1997 and the Florida Emergency Missing Child Alert in Florida.

An AMBER plan is carried out once law enforcement has been notified about an abducted child and law enforcement determines that the case meets the AMBER plan's criteria for triggering an alert. If these criteria are met, alert information is put together for public distribution. This information can include descriptions and pictures of the missing child (abductee), the suspected abductor, a suspected vehicle and any other information that may help to identify the child and suspect. The information is then faxed to radio stations designated as primary stations under the EAS. The primary stations send the same information to area radio and television stations and cable systems via the EAS and it is immediately broadcast by participating stations to millions of listeners. Radio stations may interrupt programming to announce the alert and television stations and cable systems may run a "crawl" on the screen along with a picture of the child. Some states are also incorporating electronic highway billboards in their plans. The billboards, typically used to disseminate traffic information to drivers, can alert the public of abducted children, displaying pertinent information about the child, abductor or suspected vehicle that drivers might look for on highways. The AMBER plan is described in detail on the website MissingKids.com.

Some businesses also have attempted to participate in AMBER alerts. In particular, corporations that may have a mobile workforce may be able to assist in participating in an AMBER alert. For example, SBC Communications Inc. has been reported to provide AMBER alert paging codes to technician via pagers that are worn by technician in Texas and Connecticut. However, these simple paging codes may be of limited utility. Other companies, such as America Online, have placed AMBER alert messages on their public websites. However, this placement also may have limited utility.

SUMMARY OF THE INVENTION

Embodiments of the present invention provide mobile workforce communication systems that include a mobile workforce dispatch system that is configured to dispatch the mobile workforce to perform tasks, and a plurality of wireless terminals that are carried by the mobile workforce and are configured to communicate with the mobile workforce dispatch system to allow the mobile workforce to respond to dispatches. The mobile workforce dispatch system is further configured to accept an AMBER alert notification and to broadcast a mobile workforce AMBER alert message, which comprises a description of an abductee and an identification of a location of an abduction, to the plurality of wireless terminals in response thereto so that the mobile workforce can be apprised of an AMBER alert. An AMBER gateway is configured to receive a telephone call from a member of the mobile workforce in response to a potential sighting related to an AMBER alert, and to direct the telephone call to an authority who is responsible for the AMBER alert. It will be understood that as used herein, the term AMBER alert applies to any missing person alert system whether or not it is promulgated under the AMBER plan.

In some embodiments of the present invention, the AMBER gateway is configured to receive a telephone call at a central telephone number from a member of the mobile workforce, in response to a potential sighting related to an AMBER alert. In some embodiments, the central number is *AMBER for wireless telephone calls.

In some embodiments, the AMBER gateway is configured to direct the telephone call to an authority who is responsible for the AMBER alert, based upon a geographic area of the potential sighting. In other embodiments, the AMBER gateway is configured to direct the telephone call to an authority who is responsible for the AMBER alert by directing the telephone call to an override telephone number for the AMBER alert.

In some embodiments, the AMBER gateway is further configured to disconnect itself from the telephone call from the member of the mobile workforce after directing the telephone call to the authority who is responsible for the AMBER alert. In other embodiments, the AMBER gateway comprises an interactive voice response system that is configured to receive the telephone call from the member of the mobile workforce in response to the potential sighting related to the AMBER alert, and to direct the telephone call to the authority who is responsible for the AMBER alert.

In other embodiments of the present invention, the AMBER alert messages are tailored to a geographic region where the mobile workforce is located. Thus, in some embodiments, the mobile workforce dispatch system is configured to accept an AMBER alert notification that relates to a governmental jurisdiction and is further configured to broadcast a mobile workforce AMBER alert message only to selected ones of the plurality of wireless terminals that are located in the governmental jurisdiction.

AMBER gateways according to some embodiments of the invention comprise a central telephone number that is configured to receive telephone calls from individuals in response to potential sightings related to AMBER alerts and an interactive voice response system that is configured to selectively direct telephone calls that are responsive to a selected AMBER alert to a selected authority who is responsible for the selected AMBER alert. In some embodiments, the individuals are members of a mobile workforce. In other embodiments, the individuals may be members of the general public. The telephone calls may be selectively directed based upon a geographic area of the potential sighting and/or an override telephone number for the selected AMBER alert. In other embodiments, the AMBER gateway includes a listing of telephone numbers for the authorities who are responsible for the AMBER alerts. In some embodiments, a respective telephone number in the listing is associated with a respective geographic area. In other embodiments, a respective geographic area is also associated with a respective override telephone number for an AMBER alert in the respective geographic area. In yet other embodiments, telephone calls may be selectively directed by selectively directing telephone calls that are responsive to a selected AMBER alert to a selected authority who is responsible for the selected AMBER alert based upon geographic area of the potential sighting, absent an override telephone number for the selected AMBER alert. If there is an override telephone number, then the call is directed to the override telephone number.

It will be understood that embodiments of the invention have been described above primarily with respect to mobile workforce communication systems and AMBER gateways. However, other embodiments of the invention provide mobile workforce communications methods and/or computer program products and components thereof, and methods and/or computer programs for processing sightings related to AMBER alerts.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

FIGS. 9–15 are screen shots of various graphical user interfaces that may be used according to various embodiments of the present invention.

DETAILED DESCRIPTION

Figure 1:
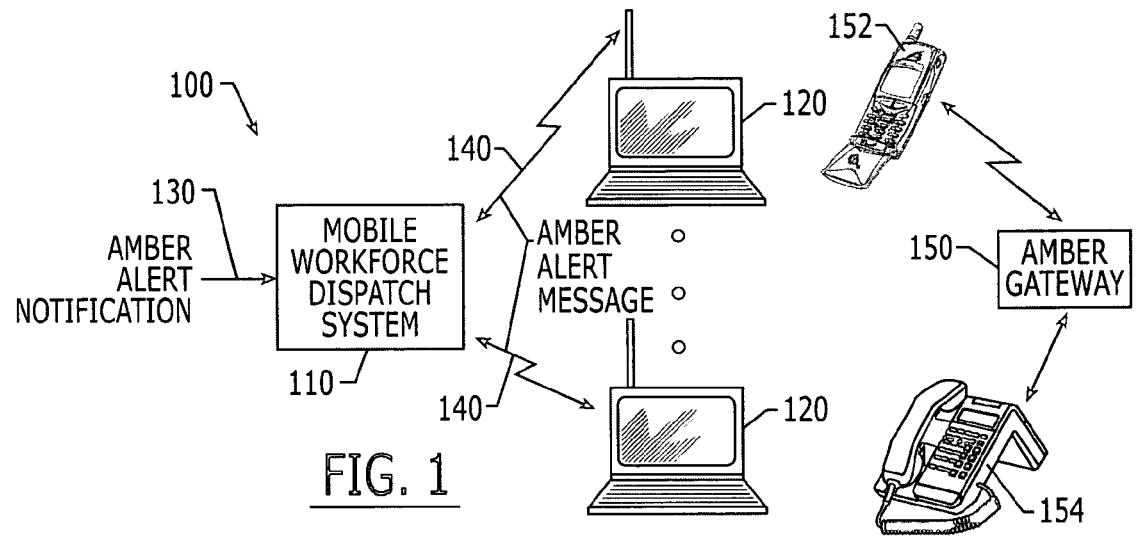
FIGS. 1–4 are block diagrams of mobile workforce communication systems, methods and/or computer program products according to various embodiments of the present invention.

The present invention now will be described more fully hereinafter with reference to the accompanying figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

FIG. 1 is a block diagram of mobile workforce communications systems, methods and/or computer program products according to various embodiments of the present invention. As shown in FIG. 1, these mobile workforce communication systems, methods and/or computer program products 100 include a mobile workforce dispatch system 110 that is configured to dispatch the mobile workforce to perform tasks. It will be understood by those having skill in the art that the mobile workforce dispatch system 110 may provide other functionality to the mobile workforce, in addition to dispatch, to allow the mobile workforce to perform their tasks while being mobile. In other embodiments, mobile workforce communication systems other than dispatch systems may be provided.

A plurality of wireless terminals 120 are carried by the mobile workforce and are configured to communicate with the mobile workforce dispatch system 110 to allow the mobile workforce to respond to dispatches. In some embodiments, the wireless terminals 120 are wireless laptop computers. However, in other embodiments, the wireless terminals 120 can include a cellular radiotelephone with a multi-line display, a Personal Communications System (PCS) terminal that may combine a cellular radiotelephone with data processing, facsimile and/or data communications capabilities, a Personal Digital Assistant (PDA) that can include a radiotelephone, pager, Internet/intranet access, Web browser, organizer, calendar and/or a Global Positioning System (GPS) receiver, and conventional laptop, palmtop and/or pervasive computing devices that include wireless receivers.

Still referring to FIG. 1, the mobile workforce dispatch system 110 is further configured to accept an AMBER alert notification 130 and to broadcast a mobile workforce AMBER alert message 140 to the plurality of wireless terminals in response to the AMBER alert notification 130, so that the mobile workforce can be apprised of an AMBER alert. The mobile workforce AMBER alert message 140 includes a description of an abductee and an identification of a location of an abduction. Other information also may be provided. An example of a mobile workforce AMBER alert message 140 will be provided below.

Continuing with the description of FIG. 1, an AMBER gateway 150 also is provided according to some embodiments of the invention. The AMBER gateway 150 is configured to receive a telephone call from a member of the mobile workforce via a wireless telephone 152 and/or a wired telephone 154, in response to a potential sighting related to an AMBER alert. The AMBER gateway 150 is also configured to direct the telephone call to an authority who is responsible for the AMBER alert. The AMBER gateway 150 may be at least partially integrated into the mobile workforce dispatch system 110 and/or the mobile workforce website 250 in some embodiments, or may be entirely distinct therefrom in other embodiments.

In some embodiments, the AMBER gateway 150 is configured to receive a telephone call at a central telephone number from a member of the mobile workforce in response to a potential sighting related to an AMBER alert. The central telephone number may be *AMBER (*26237) for wireless telephones 152 and 1-888-31AMBER (1-888-312-6237) for wired telephones 154. Other central numbers may be provided. In some embodiments, as will be described in detail below, the AMBER gateway 150 is configured to direct the telephone call to an authority who is responsible for the AMBER alert based upon a geographic area, such as a particular state of the United States, of the potential sighting. In other embodiments, the AMBER gateway 150 is configured to direct the telephone call to authorities who are responsible for the AMBER alert based upon an override telephone number. The AMBER gateway may include an interactive voice response system that interacts with the caller.

Some embodiments of the present invention stem from a recognition that it may be desirable to provide a consistent access mechanism for a member of the mobile workforce to alert the authorities as to a potential sighting related to an AMBER alert. Accordingly, some embodiments of the present invention provide a central telephone number, such as *AMBER, that may be accessed from a wireless telephone, and an interactive voice response system that can obtain information from the caller, so that the appropriate authority can be called. For example, it may be conventional for each state to run its own AMBER alert system, so that the telephone number to be called may depend on the state in which the potential sighting takes place. Moreover, in some states, the number may vary according to the alert, wherein an alert may list the name of the law enforcement agency from where the abduction case originated, and its phone numbers for responding to the alert. Other states have designated phone numbers for all responses to all AMBER alerts, regardless of their origination point.

Figure 2:
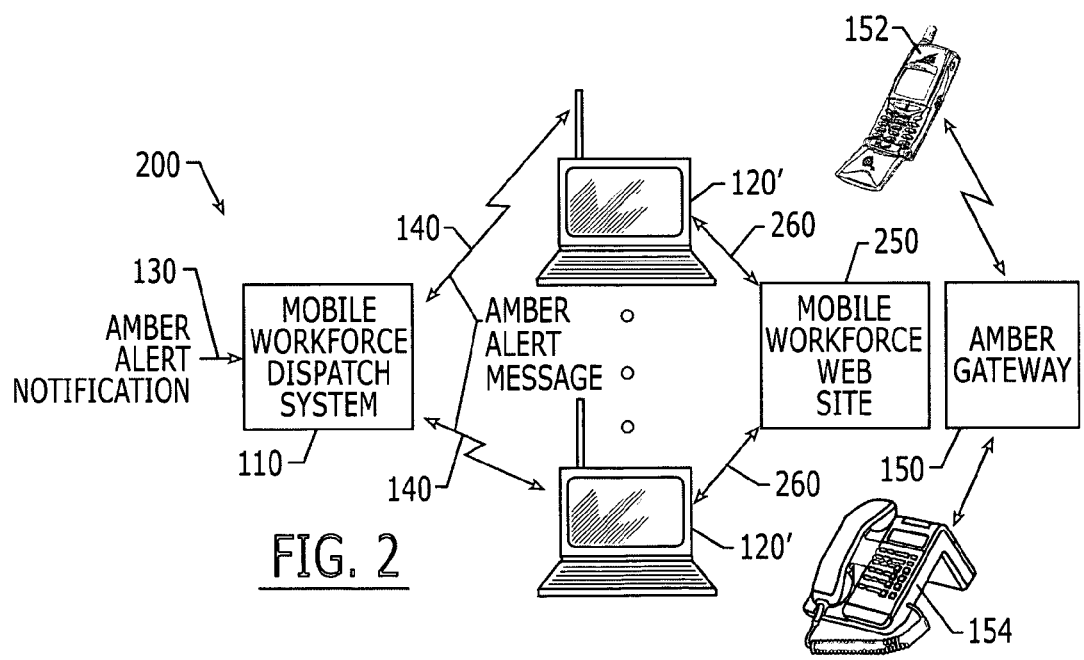

FIG. 2 is a block diagram of mobile workforce communication systems, methods and/or computer program products 200 according to other embodiments of the present invention. These mobile workforce communications systems, methods and/or computer program products 200 include a mobile workforce dispatch system 110 and a plurality of wireless terminals 120' that communicate with the mobile workforce dispatch system 110 and include Internet access. Embodiments of FIG. 2 also include a mobile workforce website 250 that is accessible by the mobile workforce using the wireless terminals 120 to assist the mobile workforce in performing tasks. The mobile workforce website 250 is further configured to allow the mobile workforce to access the website 250 from the plurality of wireless terminals 120 in response to the mobile workforce AMBER alert message 140, to obtain additional information concerning the AMBER alert. The access connection 260 between the wireless terminals 120 and the mobile workforce website may be wired, optical and/or wireless. In some embodiments, the mobile workforce AMBER alert message also includes an identification of the mobile workforce website 250, for example the Uniform Resource Locator (URL) of the mobile workforce website 250. An AMBER gateway 150 also is provided as was described above.

The mobile workforce website 250 may provide various amounts of information in various embodiments of the present invention, which may depend upon the amount of information that is provided in the AMBER alert message 140 itself. Moreover, in other embodiments of the present invention, the AMBER alert message 140 may provide the entire AMBER alert, and the mobile workforce website 250 need not be used for AMBER alerts. More specifically, in some embodiments, the AMBER alert message 140 may be a shortened version of the actual AMBER alert, and may refer the mobile workforce to the mobile website for the alert in its entirety and/or to access a photograph that may accompany the alert. In other embodiments, the AMBER alert may be delivered to the mobile workforce in its entirety via the AMBER alert message 140, and the mobile workforce may only need to access the mobile workforce website 250 when the alert states that a photograph is available. In still other embodiments, the AMBER alert message 140 may also comprise a photograph, when available, so that the mobile workforce website 250 need not be accessed for an AMBER alert.

In other embodiments of the present invention, the mobile workforce dispatch system 110 is configured to accept an AMBER alert notification 130 that relates to a governmental jurisdiction, such as a particular state of the United States. The mobile workforce dispatch system 110 is further configured to broadcast a mobile workforce AMBER alert message 140 only to selected ones of the plurality of wireless terminals 120/120' that are located in the related governmental jurisdiction (for example, located in the related state). Accordingly, only those members of the wireless workforce that have a high likelihood of participating in an AMBER alert may be notified of the AMBER alert. In other embodiments of the invention, the AMBER alert notification 130 is an AMBER alert email message from a law enforcement authority. In these embodiments, the mobile workforce dispatch system 110 is further configured to convert the AMBER alert email message into the mobile workforce AMBER alert message 140. Conversion may be automatic or may include manual operations as will be described below.

Figure 3:
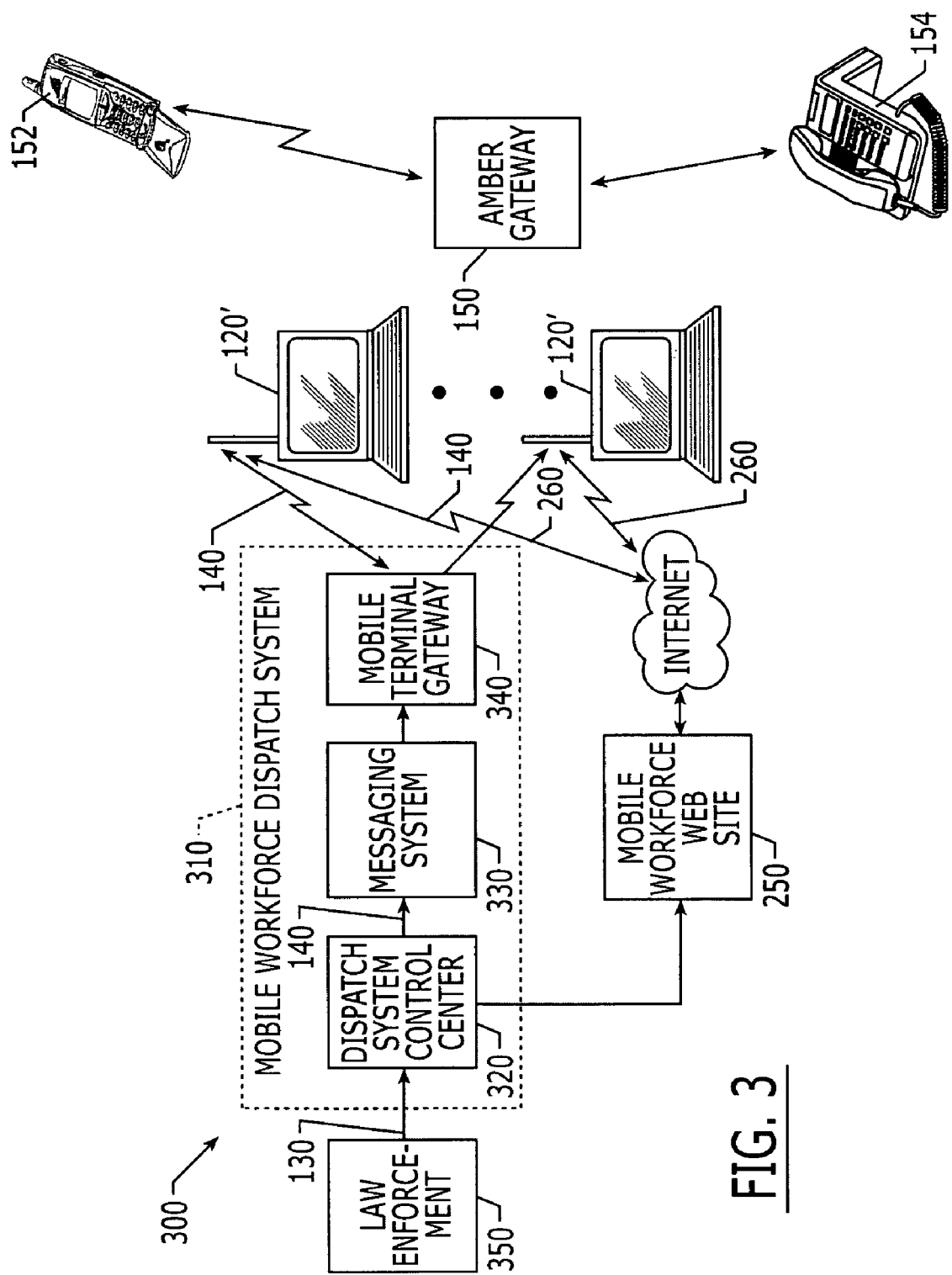

FIG. 3 is a block diagram of other mobile workforce communication systems, methods and/or computer program products according to other embodiments of the invention. These systems, methods and/or computer program products 300 include a mobile workforce dispatch system 310 that includes at least four component parts: a dispatch system control center 320, a messaging system 330, a mobile terminal gateway 340 and an AMBER gateway 150. The dispatch control center 320 is configured to monitor and control the mobile workforce dispatch system 310. In these embodiments, an AMBER alert notification 130 in the form of an email message may be obtained from a law enforcement agency 350. The dispatch control center 320 is configured to accept the AMBER alert email message 130 from the law enforcement agency 350 and is further configured to convert the AMBER alert email message 130 into the mobile workforce AMBER alert message 140. The messaging system 330 is configured to distribute the AMBER alert notification message 140 as appropriate. The mobile terminal gateway 340 is configured to provide a gateway for bidirectional communications with the wireless terminals 120/120' including communication of the AMBER alert message. The AMBER gateway 150 also is provided as was described above. A mobile workforce website 250 may be provided in some embodiments, but may not be used in other embodiments, as was described above.

Figure 4:
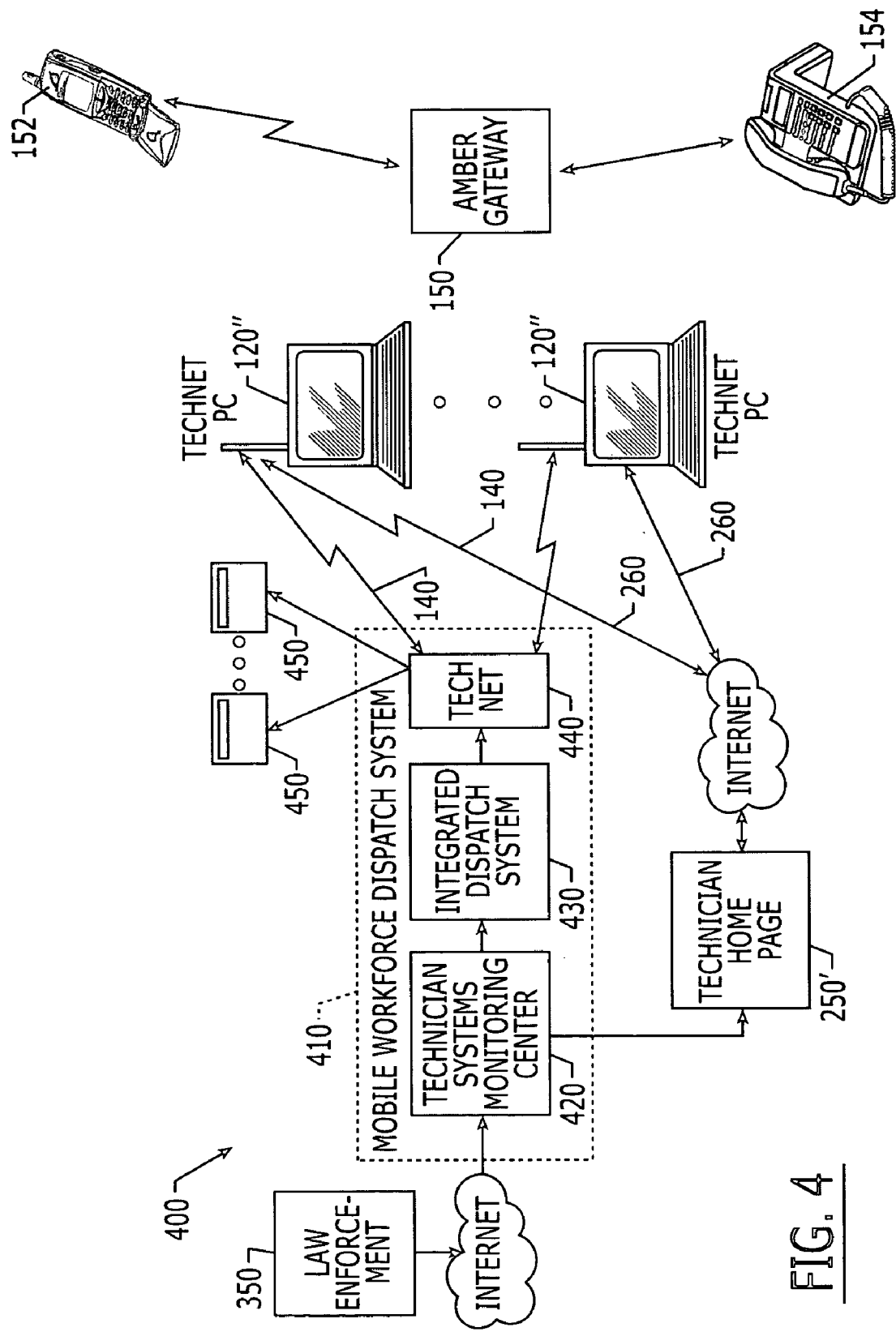

FIG. 4 illustrates other embodiments of mobile workforce communication systems, methods and/or computer program products according to the present invention. In these mobile workforce communication systems, methods and/or computer program products 400, the dispatch control center 320 is referred to as a Technician Systems Monitoring Center (TSMC) 420, and the messaging system 330 is referred to as an Integrated Dispatch System (IDS) 430. The mobile terminal gateway is referred to as TechNet 440 and the wireless terminals are referred to as TechNet PCs 120" to conform to conventions that are used in the telecommunications industry for communicating with a mobile workforce of telephone technicians. The mobile workforce website 250 is also referred to as a technician home page 250'. As was described above, the technician home page 250' may be used in some embodiments, but may not be needed in other embodiments of the present invention. As also shown in FIG. 4, a mobile workforce may be provided with a paging code that signifies an AMBER alert on unidirectional pagers 450. An AMBER gateway 150 also is provided as was described above. It will be understood that pagers 450 may be added to the embodiments of FIGS. 1–3 as well.

In still other embodiments of the present invention, the mobile workforce dispatch system 110, 310, or 410 is further configured to accept an AMBER alert cancellation notification and to broadcast an AMBER alert cancellation message to the plurality of wireless terminals 120, 120', 120" in response thereto. Alert cancellation may be provided in any of the embodiments described herein.

Embodiments of the present invention can provide an AMBER alert message to a mobile workforce that can contain sufficient useful information for the mobile workforce to respond to the AMBER alert. Accordingly, the AMBER alert message includes at least a description of an abductee and an identification of a location of an abduction. The AMBER alert message also can include a description of a vehicle and identification of the mobile workforce website where more information about the abduction can be obtained. Thus, the mobile workforce can immediately have at their disposal sufficient information to identify a person that may be involved in an abduction. In some embodiments, the AMBER alert message is a text message of up to 320 characters. In other embodiments, an image also may be included. Embodiments of the present invention can also provide a central interface which may be called by a member of the mobile workforce who has a potential AMBER sighting. Separate telephone numbers for each state and/or AMBER alert need not be memorized by individuals, and computer access may not be needed to report an AMBER sighting or to determine a telephone number to report an AMBER sighting.

The mobile workforce website 250 and/or the technician home page 250' can include complete information on the AMBER alert. After receiving the AMBER alert message at the wireless terminal 120, 120', 120", a member of the mobile workforce can log on to the mobile workforce website 250 or technician home page 250' to obtain additional information about the AMBER alert. Moreover, as was described above, in some embodiments, the AMBER alert notification message 140 can include complete information on the AMBER alert, so that the mobile workforce website 250 or technician home page 250' need not be used to obtain additional information about the AMBER alert. As was also described above, in some embodiments, all the text information on the AMBER alert may be contained in the AMBER alert notification message 140, and the mobile workforce website 250 or technician home page 250' may only be used to obtain a photograph, if desired.

Additional embodiments of the present invention will now be described with reference to FIG. 4. These embodiments include a mobile workforce dispatch system 410 that includes a Technician Systems Monitoring Center (TSMC) 420, an Integrated Dispatch System (IDS) 430, a TechNet system 440, TechNet PCs 120" and a technician home page 250' to conform to terminology that is used in the telecommunications industry. However, it will be understood that the embodiments that will be described below also are applicable to embodiments of FIGS. 1–3.

Figure 5:
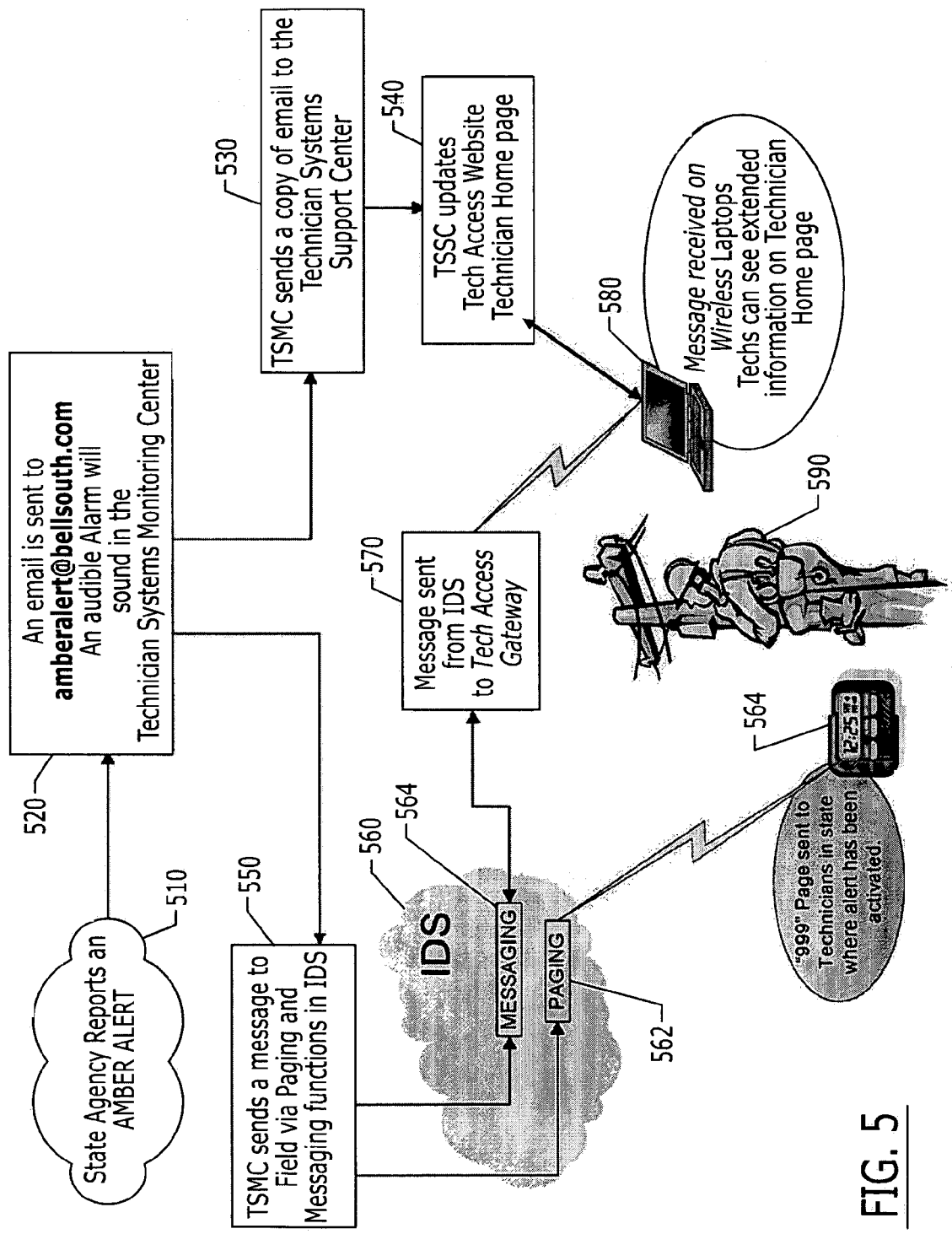
FIG. 5 is a block diagram that illustrates operations that may be performed by systems, methods and/or computer program products according to embodiments of the present invention.

FIG. 5 is a block diagram that illustrates operations that may be performed by systems, methods and/or computer program products according to embodiments of the present invention. As shown in FIG. 5 at Block 510, a state agency reports an AMBER alert by sending an email at Block 520 to a prescribed email address that is located at the TSMC. In some embodiments, as also shown in Block 520, an audible alarm will sound in the TSMC. At Block 530, the TSMC sends a copy of the email to a Technician Systems Support Center (TSSC), which is responsible for maintaining the technician home page. The TSSC updates the technician home page, also referred to as a Tech Access Website, at Block 540. Moreover, as was described above, in other embodiments of the present invention, the technician home page need not be updated, so that the operations of Blocks 530 and 540 need not be performed.

Referring again to Block 520, prior to, after, or simultaneously with sending the copy of the email to the TSCC at Block 530, the TSMC also sends a message to the mobile workforce, here, field technician, at Block 550 via the paging and messaging functions in the IDS 560. The paging function 562 sends a page to pagers 564. For example, a numeric "999" page or an alphanumeric "999_AMBER" page is sent to technician in the state where the alert has been activated. The messaging function 564 sends a message from IDS 560 to the Tech Access Gateway at Block 570. This message is received on the wireless laptops 580. The technician 590 can also see extended information on the technician home page at Block 540, or may see all of the information as part of the message that is sent from the Tech Access Gateway at Block 570, to the wireless laptops at Block 580. In yet other embodiments, the technician can see the entire AMBER alert from the message sent from the IDS to the Tech Access Gateway, and may view a photograph at the technician home page. Upon a potential sighting related to an AMBER alert, the technician 590 can use the technician's cell phone or a wire line phone to call a central telephone number and interact with the AMBER gateway, to be directed to the appropriate authority who is responsible for the AMBER alert.

Figure 6:
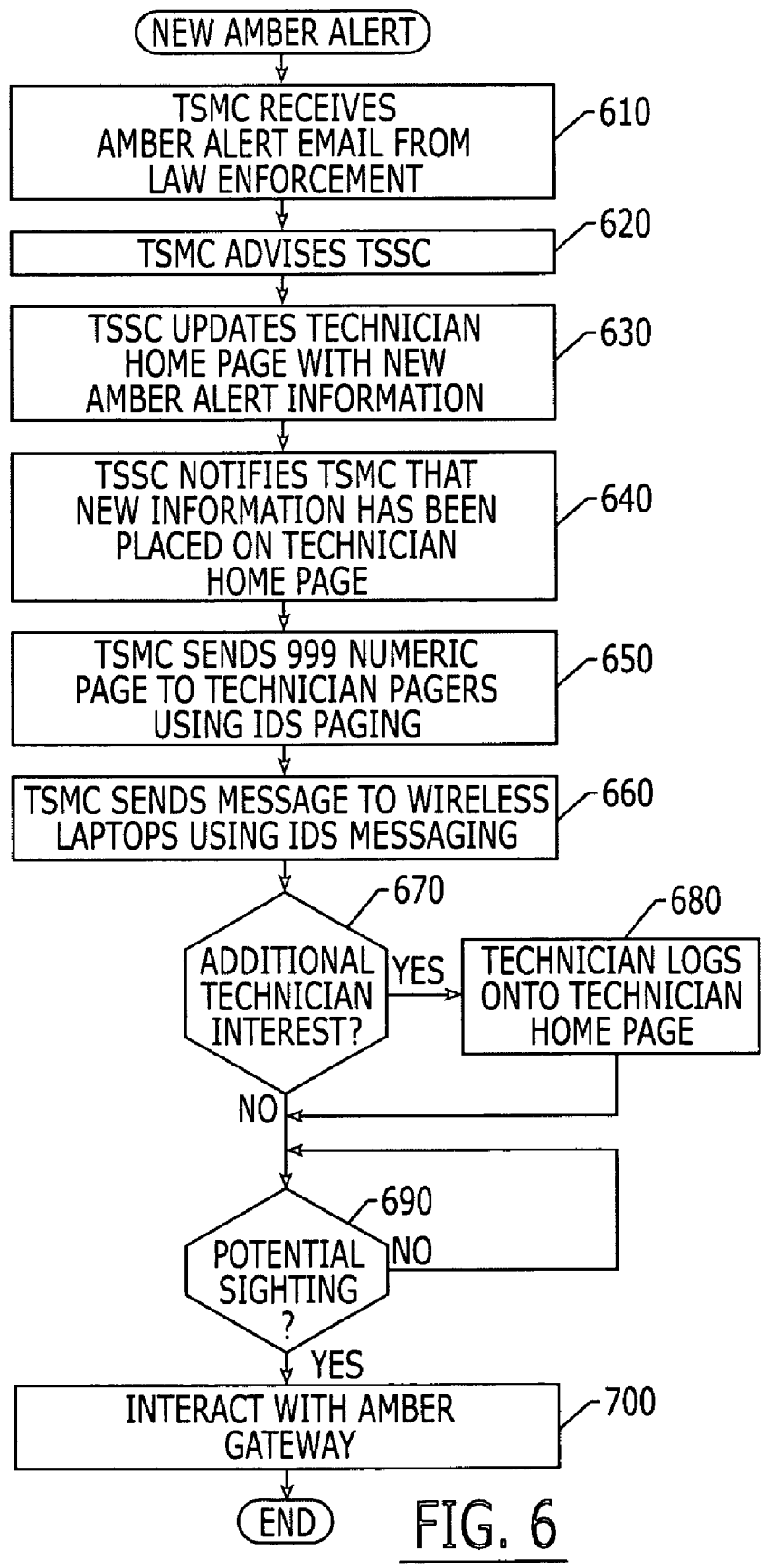
FIGS. 6–8 are flowcharts of operations that may be performed to provide a new AMBER alert, to update an AMBER alert and to cancel an AMBER alert, respectively, according to embodiments of the present invention.

FIG. 6 is a flowchart of operations that may be performed by mobile workforce communications systems, methods and/or computer program products according to some embodiments of the present invention to provide a new AMBER alert. These operations may be performed by, for example, systems, methods and/or computer program products of FIGS. 1–5. As shown in FIG. 6 at Block 610, the TSMC receives an AMBER alert email from law enforcement. At Block 620, the TSMC advises the TSSC. At Block 630, the TSSC updates the technician home page with the new AMBER alert information. At Block 640, the TSSC notifies the TSMC that the new information has been placed on the technician home page. In other embodiments of the present invention, the operations of Blocks 620, 630 and 640 need not be performed. At Block 650, the TSMC sends a 999 numeric page to the technician pagers using IDS paging function, and at Block 660, the TSMC sends a message to the wireless laptops using the IDS messaging function. In some embodiments, the message may have a maximum of 360 characters and may include the location of the alert, a brief description of the child and the URL of the home page. In other embodiments, the message may be longer and may include the entire alert. In some embodiments, the message may include a photograph. In other embodiments, a photograph may be accessed at the technician home page. At Block 670, if the technician has additional interest in finding out about the AMBER alert, for example, because the technician is proximate to the location, then the technician logs onto the technician home page at Block 680. In other embodiments, the technician need not access the technician home page, because the entire AMBER alert is provided in the message, so that operations of Blocks 670 and 680 need not be performed.

Continuing with the description of FIG. 6, upon a potential sighting by the technician at Block 690, the technician can interact with the AMBER gateway at Block 700 in order to be directed to the authority who is responsible for the AMBER alert. Additional details of this interaction will be described below.

Figure 7:
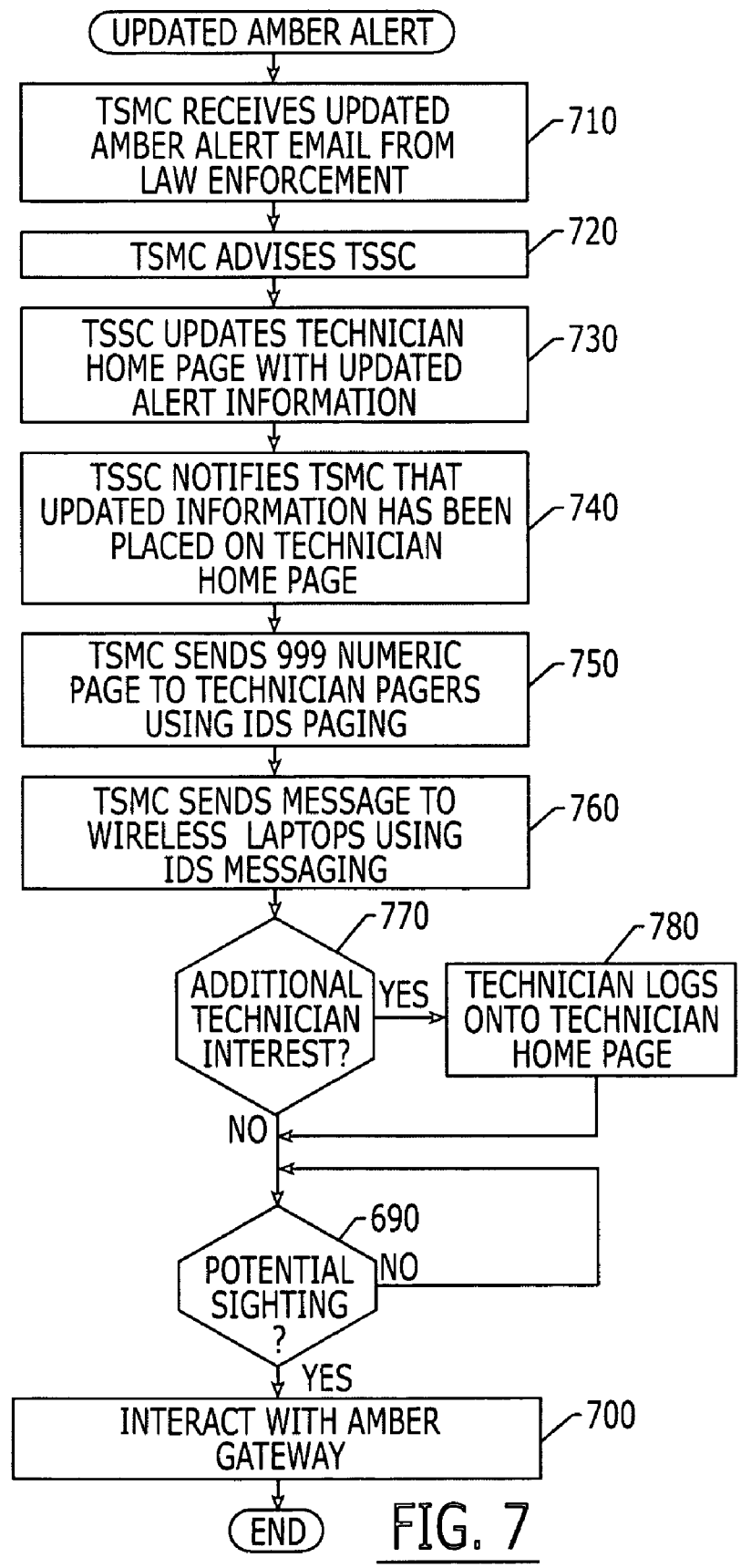

FIG. 7 is a flowchart of operations that may be performed to update an AMBER alert. These operations may be performed using systems, methods and/or computer program products of FIGS. 1–5, for example. Referring to FIG. 7, at Block 710, the TSMC receives an updated AMBER alert email from law enforcement. At Block 720 the TSMC advises the TSSC. At Block 730, the TSSC updates the technician home page with updated alert information. At Block 740, the TSSC notifies the TSMC that the updated information has been placed on the technician home page. However, as was described above, in other embodiments of the present invention, the technician home page need not be updated, so that the operations of Blocks 720, 730 and 740 need not be performed. At Block 750 the TSMC sends a 999 numeric page using the IDS paging function, and at Block 760, the TSMC sends a message to the wireless laptops using the IDS messaging. The IDS message may include the updated information and the technician home page URL. At Block 770, if the technician has additional interest then the technician logs on to the technician home page at Block 780. However, as was described above, in other embodiments of the present invention, the operations of Blocks 770 and 780 need not be performed. Upon potential sighting by a technician at Block 690, the technician can interact with the AMBER gateway at Block 700, as will be described in detail below.

Figure 8:
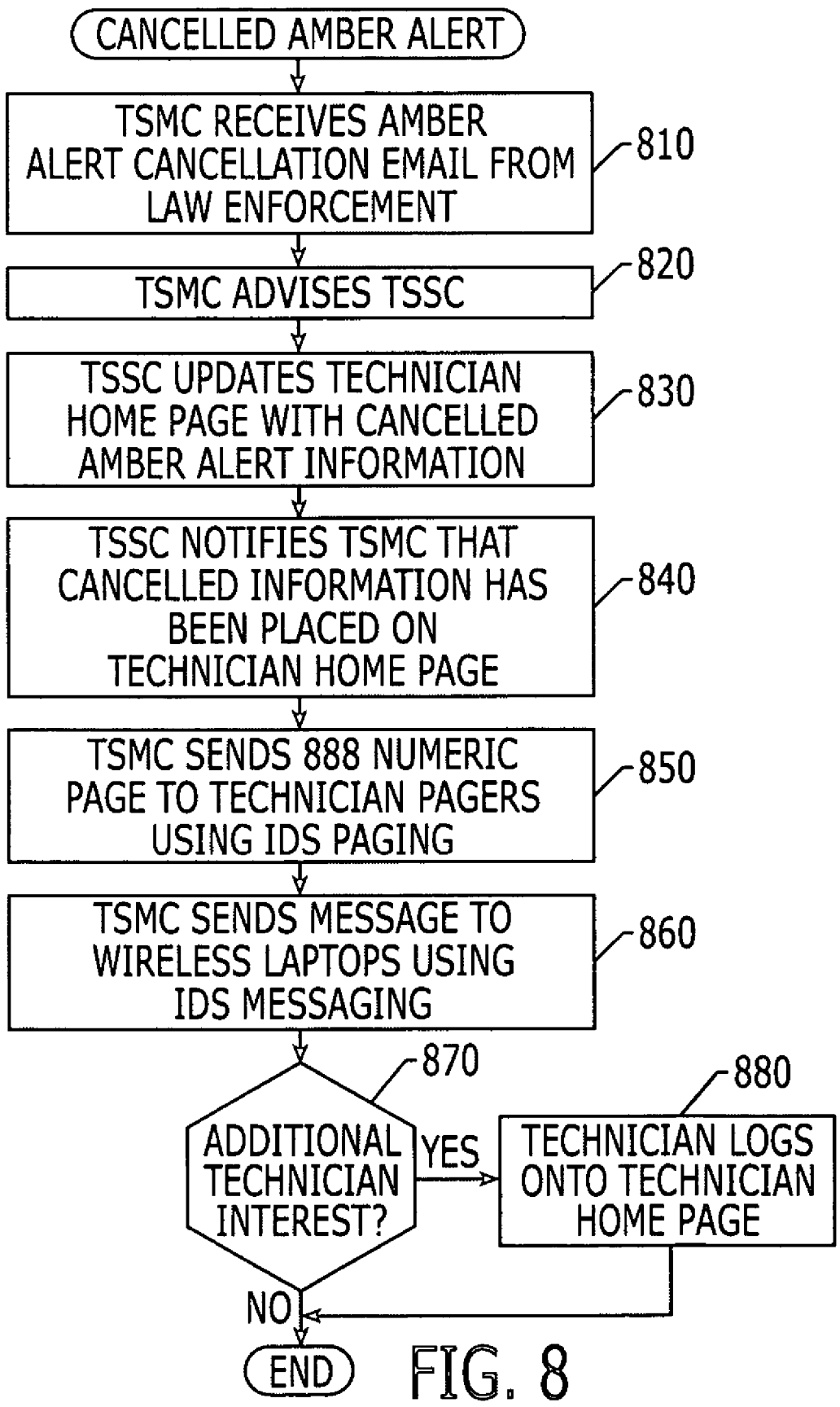

FIG. 8 is a flowchart of operations that may be performed to cancel an AMBER alert according to some embodiments of the present invention. These operations may be performed by systems, methods and/or computer program products of FIGS. 1–5. As shown in FIG. 8, the TSMC receives an AMBER alert cancellation email from law enforcement at Block 810 and the TSMC advises the TSSC at Block 820. The TSSC updates the technician home page with the cancelled alert information at Block 830 and the TSSC notifies the TSMC that the cancelled information has been placed on the technician home page. However, as was described above, in other embodiments of the invention, the operations of Blocks 820, 830 and 840 need not be performed. At Block 850, the TSMC sends an "888" numeric page or an "888_amber" alphanumeric page to the technician pagers using IDS paging. At Block 860, the TSMC sends a message to the wireless laptops using IDS messaging. The message can include the cancelled information and present page URL. At Block 870 if the technician desires additional information, the technician logs on to the technician home page at Block 680. However, as was described above, in other embodiments of the present invention, the operations of Blocks 870 and 880 need not be performed.

Additional discussion of systems, methods and computer program products according to embodiments of the present invention will now be provided. Screen shots that may be used in a wireless terminal 120, 120', 120" or 580 and on a technician home page 250, 250' or 540, according to embodiments of the invention, also will be provided.

Figure 10:
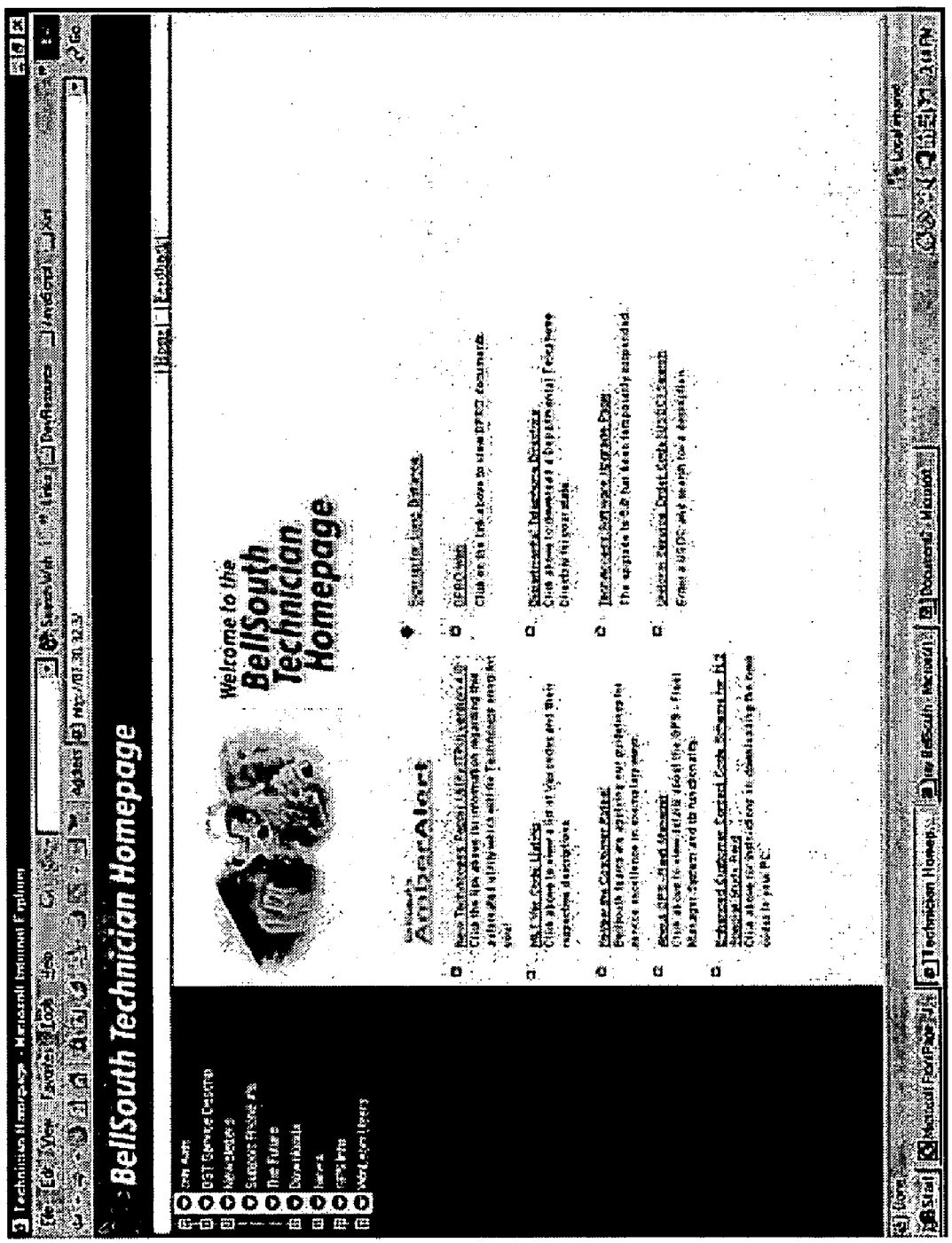
Figure 11:
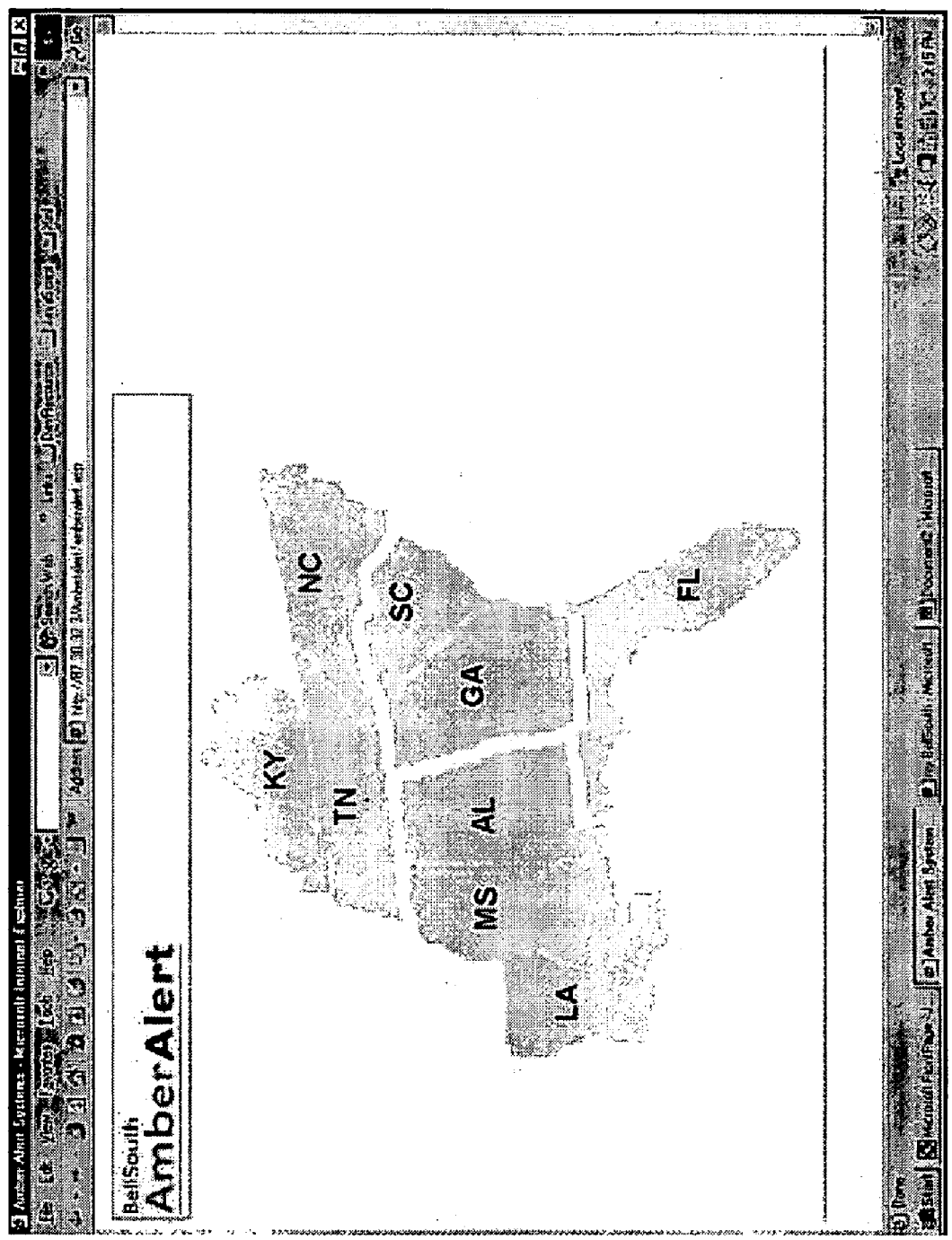
Figure 12:
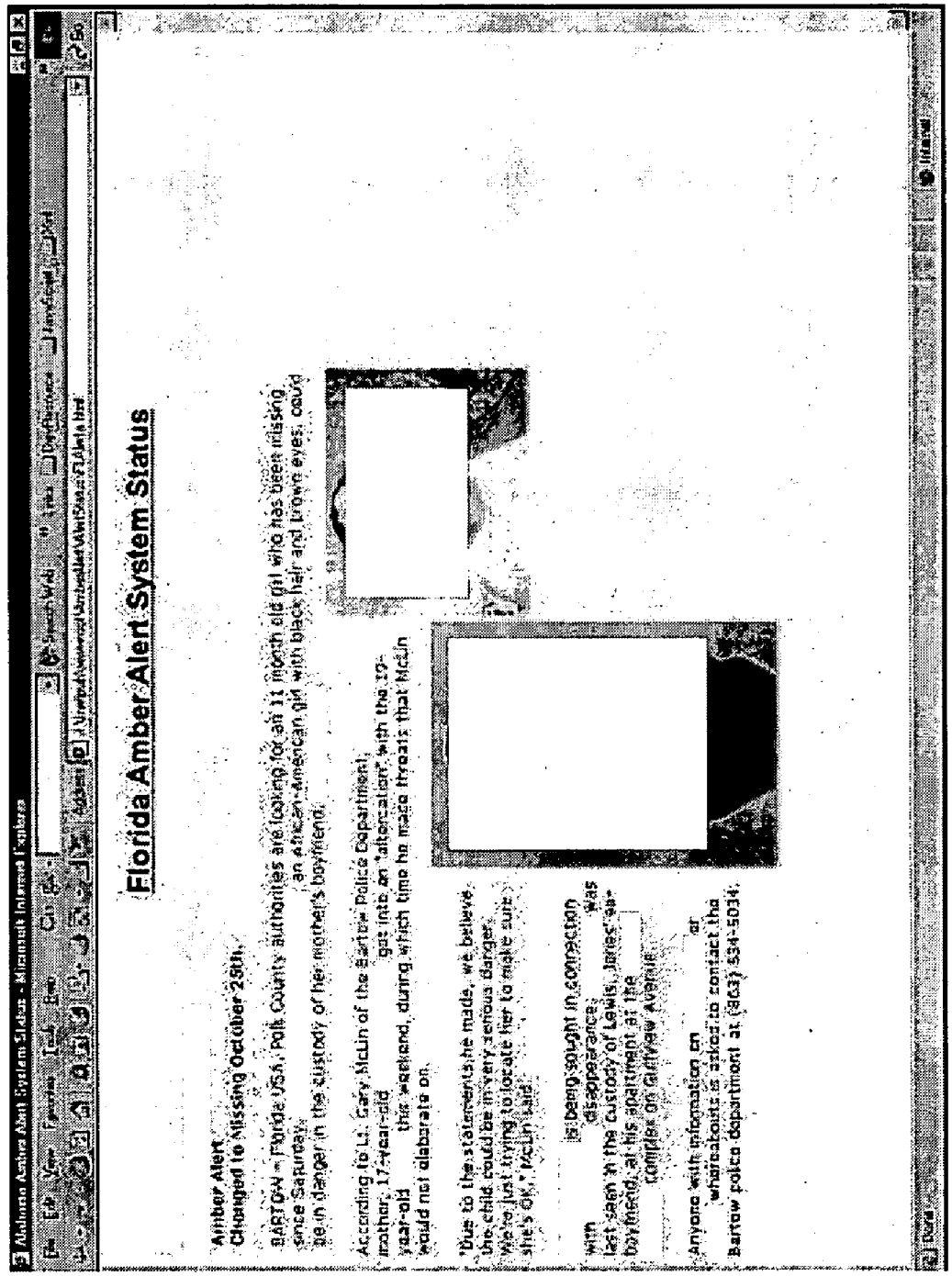

As was described extensively above, an AMBER alert notification may be obtained by the mobile workforce dispatch system as an email message from law enforcement authorities. A screen shot of an AMBER alert message that may be obtained from law enforcement authorities is shown in FIG. 9. As was also described extensively above, in some embodiments of the invention, a mobile workforce website may be updated to place the AMBER alert thereon. However, in other embodiments of the present invention, the entire AMBER alert message of FIG. 9 may be provided to the wireless terminals. For example, FIG. 10 illustrates a technician home page which includes an AMBER alert link thereon. Upon selecting the AMBER alert link, a map of FIG. 11 may be provided to allow the technician to select the technician state. Upon selection of the state, the AMBER alert of FIG. 12 may be displayed. In FIG. 12, the photographs have been partly concealed and the names have been concealed for privacy.

The AMBER alert message that is provided to the wireless terminals and/or on the technician home page (FIG. 12) may correspond identically to the AMBER alert email message that was obtained from law enforcement authorities (FIG. 9) in some embodiments. In other embodiments, personnel at the TSMC or elsewhere may manually compose a new AMBER alert message in a predetermined format based on the email message that is received from law enforcement authorities. In still other embodiments, the email message that is received from law enforcement authorities may be automatically converted into a predetermined format of an AMBER alert message that is provided to the wireless terminals and/or placed on the technician home page. Accordingly, manual and/or automatic conversion of the AMBER alert email message that is obtained from law enforcement authorities to the AMBER alert message on the wireless terminals and/or technician home page may be provided.

Figure 13:
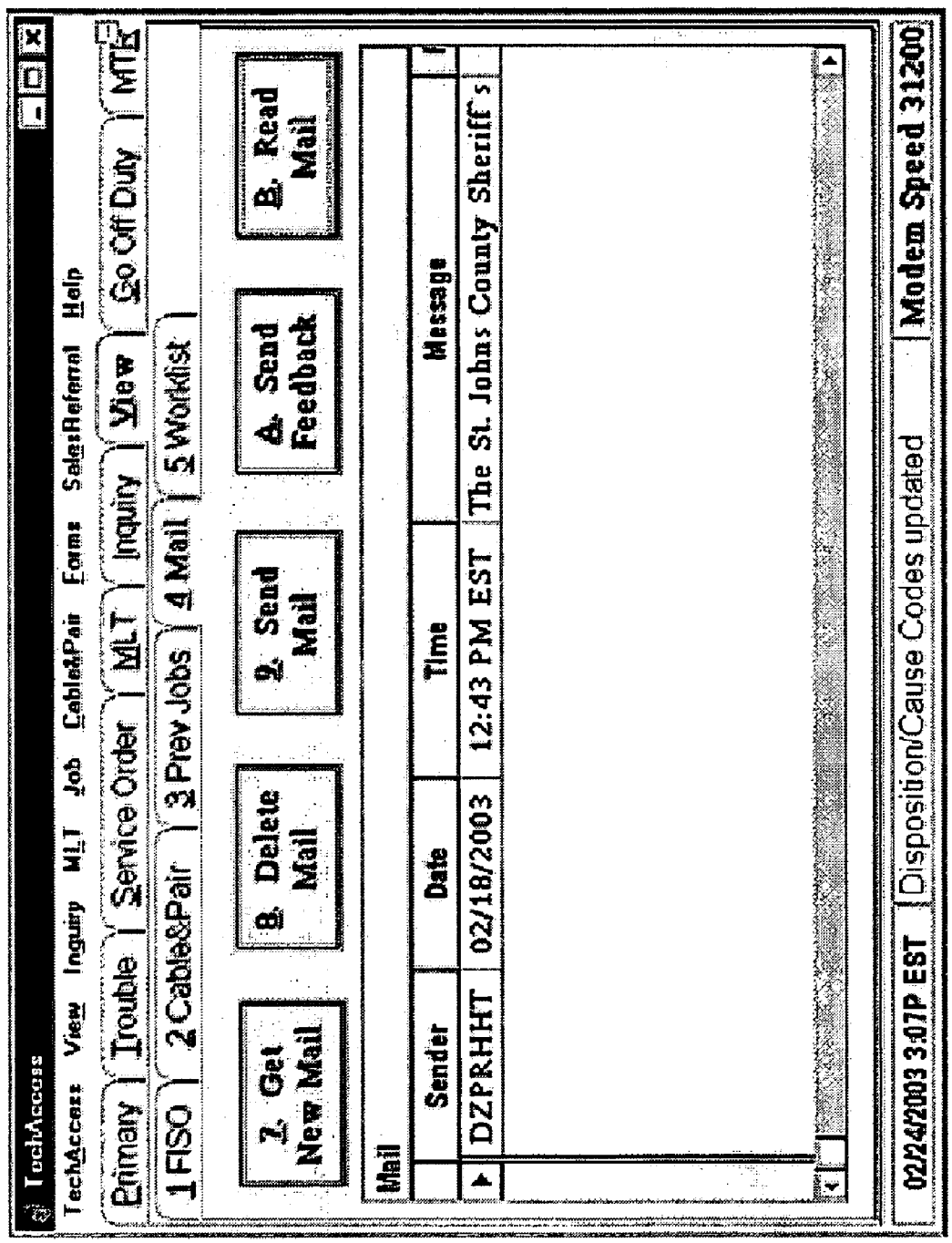
Figure 14:
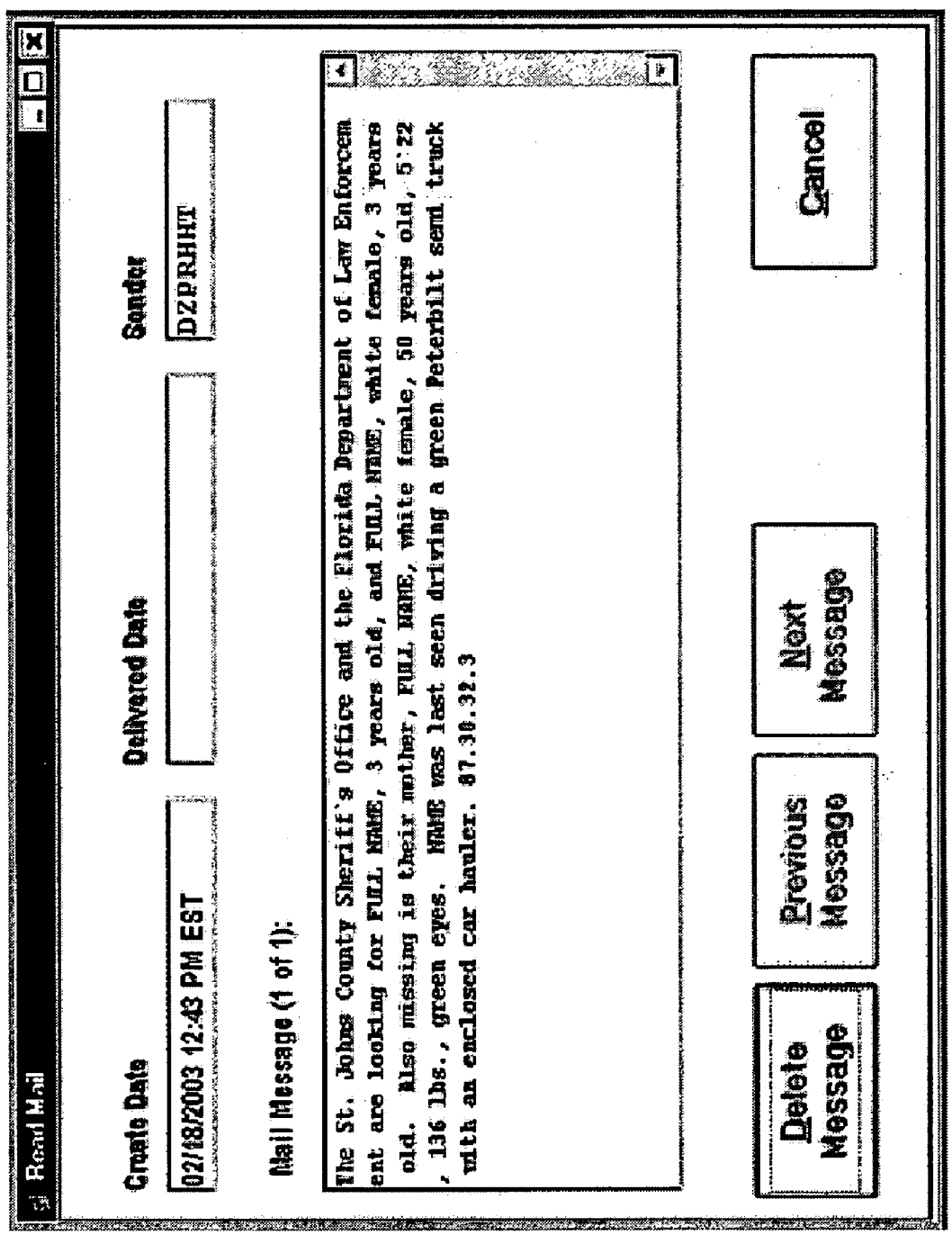

As was also described extensively above, a mobile workforce AMBER alert message may be sent to the plurality of wireless terminals in response to the AMBER alert. A computerized automated voice message or other mechanism may inform the technician that new mail is present, in some embodiments. FIG. 13 illustrates an example of a mobile workforce AMBER alert message that is received as a "new mail" message or a special AMBER alert message. FIG. 14 illustrates an example of a mobile workforce AMBER alert that may be displayed on the wireless terminal. As was described above, in other embodiments of the present invention, the entire AMBER alert message, such as was illustrated in FIG. 9 and/or FIG. 12, may be displayed on the wireless terminal.

As was described above, the mobile workforce AMBER alert message (FIG. 14) may be generated automatically and/or manually from the email that is received from law enforcement authorities (FIG. 9) by personnel of the TSMC and/or others. The mail message may be delivered the next time the technician closes, returns or gets a new job. The technician can then take the opportunity to access the technician home page (FIG. 10). This may be done by logging in to the technician home page using a landline (wired) connection. The AMBER alert on the technician home page (FIG. 12) can include the telephone number of the law enforcement agency that should be contacted in the event the individuals or vehicles described in the alert are observed. As was described above, in other embodiments of the present invention, the entire AMBER alert message, such as was illustrated in FIG. 9 and/or FIG. 12, may be displayed on the wireless terminal.

It will be understood that the technician role in the AMBER alert network is that of supplying additional awareness and support for an effective community service program. Generally, a technician should avoid anything that would be dangerous to their person or their equipment as well as any personal involvement beyond simply alerting law enforcement agencies. Moreover, accessing the technician home page to view the entire AMBER alert, if necessary or desirable, should be performed at the next available opportunity rather than disrupting normal work duties.

In other embodiments of the present invention, a work management center ("WMC") management team, which is responsible for managing the mobile workforce, also may be notified of the AMBER alert via the IDS 430. The WMC can provide additional awareness and support and/or provide detailed information to technician who are unable to view the technician home page.

Figure 15:
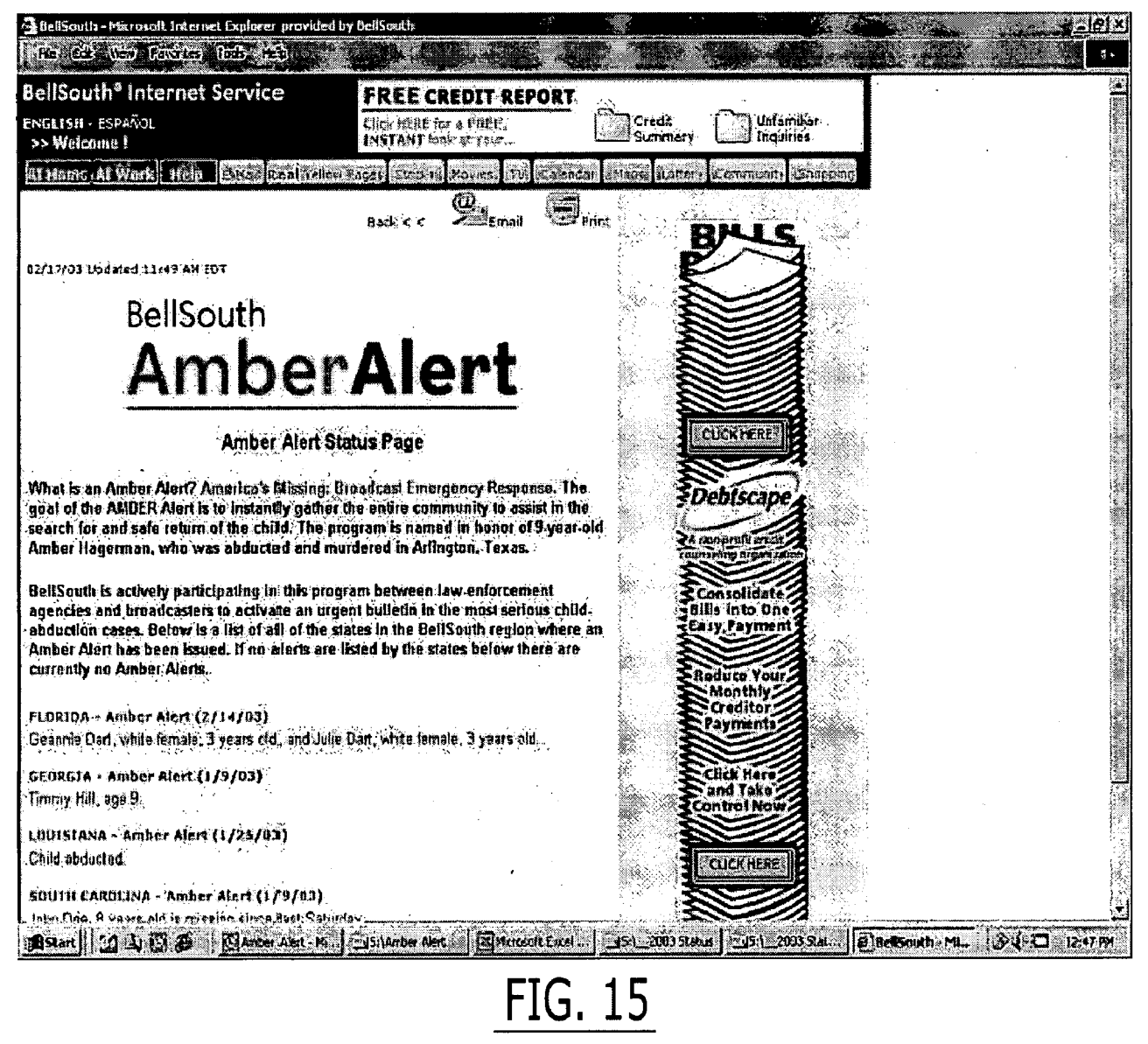

In still other embodiments, the TSMC staff and/or others can also send an AMBER alert message to a website that is available to individuals or entities other than the mobile workforce. An example is shown in FIG. 15. This website may post the information to let customers or others know that the alert has been issued. In some embodiments, the alert may be left on this site for 24 hours and treated the same as a breaking news story.

Accordingly, embodiments of the present invention can allow an AMBER alert to be efficiently broadcast to a mobile workforce. The mobile workforce may be in an ideal position to provide the authorities with information to resolve the AMBER alert.

Portions of FIGS. 1–15 are also described in application Ser. No. 10/388,335 to Dennis et al., entitled Systems, Methods and Computer Program Products for Communicating Amber Alerts to a Mobile Workforce, filed Mar. 13, 2003, and assigned to the assignee of the present invention, the disclosure of which is hereby incorporated herein by reference in its entirety as if set forth fully herein.

Figure 16:
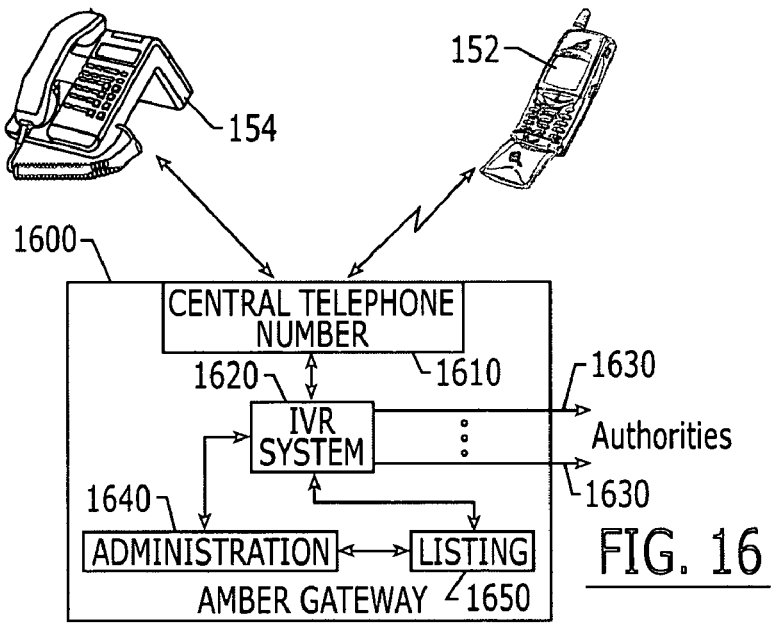
FIG. 16 is a block diagram of an AMBER gateway according to embodiments of the present invention.

FIG. 16 is a block diagram of AMBER gateways, such as AMBER gateways 150 of FIGS. 1–4, according to various embodiments of the present invention. As shown in FIG. 16, an AMBER gateway 1600 can include a central telephone number 1610 that is configured to receive telephone calls from individuals in response to potential sightings related to AMBER alerts. As was described above, the central telephone number may be different for wireless telephones 152 and wired telephones 154. For wireless telephones, the central telephone number may be *AMBER, and for wired telephones 154, the central telephone number may be 1-888-31AMBER. Other central telephone numbers may be provided. An Interactive Voice Response (IVR) system 1620 is configured to selectively direct telephone calls that are responsive to a selected AMBER alert to a selected authority 1630 who is responsible for the selected AMBER alert. An administration system 1640 also may be provided, that allows the IVR system to be maintained. The administration system may include a listing 1650 of the appropriate telephone numbers for the appropriate authority, as will be described in detail below.

IVR systems are well known to those having skill in the art, and need not be described further herein. Moreover, the functionality of the IVR system 1620, administration system 1640, and/or listings 1650 may be provided by one or more modules which may include general purpose hardware, special purpose hardware and/or software.

Figure 17:
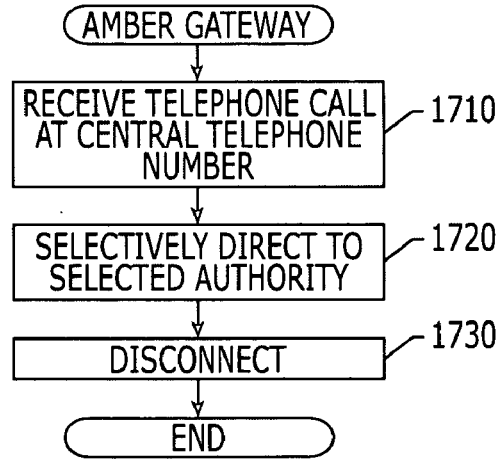
FIGS. 17 and 18 are flowcharts of operations that may be performed by AMBER gateways according to various embodiments of the present invention.

FIG. 17 is a flowchart of operations that may be performed by an AMBER gateway, such as an AMBER gateway 150 of FIGS. 1–4 and/or 1600 of FIG. 16, to process potential sightings related to AMBER alerts as was generally described at Block 700 of FIGS. 6–7. Referring to FIG. 17, at Block 1710, telephone calls are received from callers in response to potential sightings related to AMBER alerts, at a central telephone number. In some embodiments, the AMBER gateway may operate in connection with mobile workforce communications systems, methods and/or computer program products, so that the callers are members of the mobile workforce. However, in other embodiments of the invention, an AMBER gateway may be accessible by members of the general public, so that the telephone calls may be received at a central number at Block 1710 from a member of the general public.

Still referring to FIG. 17, at Block 1720, telephone calls that are responsive to a selected AMBER alert are selectively directed to a selected authority who is responsible for the selected AMBER alert. Accordingly, even though a given state may have its own AMBER alert number and/or an individual AMBER alert may have its own number, a caller may call a central number and then be directed to the appropriate authority.

Still referring to FIG. 17, in some embodiments of the present invention, at Block 1730, after selectively directing at Block 1720, the telephone call is disconnected from the central telephone number. This disconnecting may be referred to as a "blind transfer", wherein once the connection is made between the individual who has the potential sighting and the appropriate authority, the AMBER gateway 150 is dropped from the loop, so that the AMBER gateway 150 can receive other calls on that telephone line.

Figure 18:
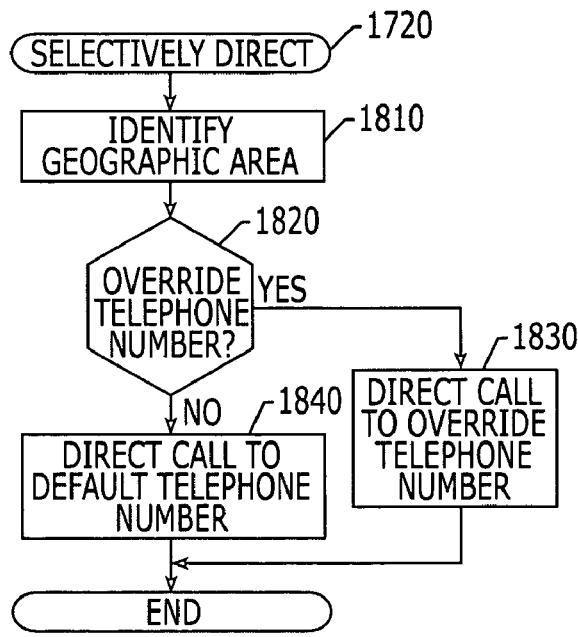

FIG. 18 is a flowchart of operations that may be performed by an AMBER gateway, such as an AMBER gateway 150 or 1600, to selectively direct telephone calls that are responsive to a selected AMBER alert to a selected authority who is responsible for the selected AMBER alert, as was generally described, for example, at Block 1720 of FIG. 17. In particular, as shown in FIG. 18, the IVR system, such as the IVR system 1620 of FIG. 16, may be used to allow the caller to identify a geographic area such as a state of the United States, at Block 1810. A determination is then made at Block 1820 as to whether there is an override telephone number in the AMBER alert gateway for the identified geographic area.

Figure 19:
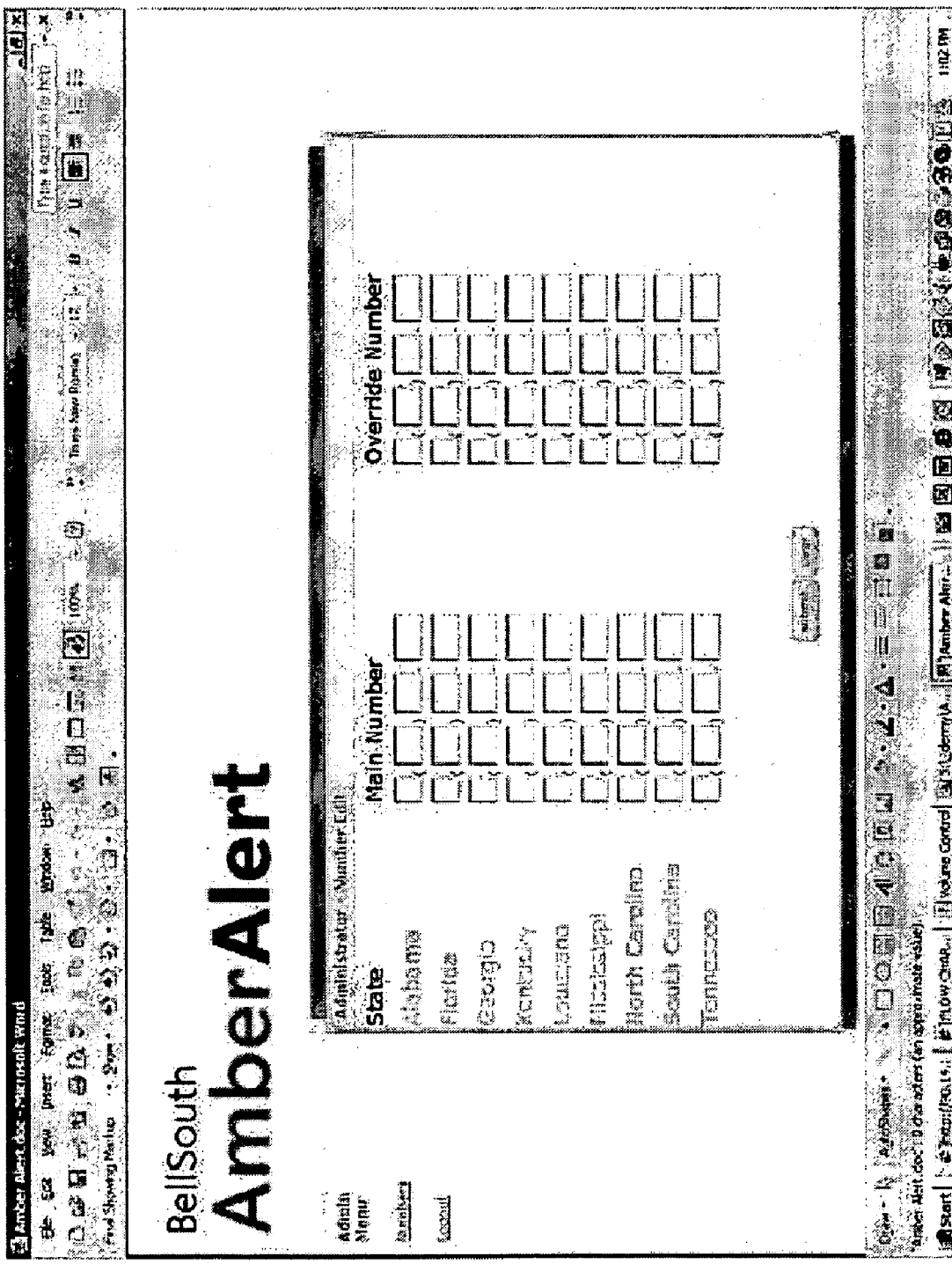
FIG. 19 is a screen shot of a graphical user interface that may be provided by an AMBER gateway according to embodiments of the present invention.

In particular, as was described above, in some states, the contact number for an AMBER alert can vary according to the alert, wherein an alert can list the name of the law enforcement agency from where the child abduction case originated and its phone number for responding to the alert. Other states have designated phone numbers for all responses to AMBER alerts, regardless of their origination point. According to some embodiments of the invention, a listing, such as the listing 1650, may be provided in an AMBER gateway, such as the AMBER gateway 1600. A user interface for an exemplary listing is shown in FIG. 19. As shown in FIG. 19, for each state, a main or default telephone number and an override telephone number may be provided. The main number is the default number which is used for an AMBER alert in the state, unless an override number is present. The override number can be used to provide a contact number for a specific AMBER alert while that AMBER alert is present in that state. Techniques for populating the listing will be described below in connection with FIG. 20.

Thus, returning to FIG. 18, if an override telephone number is present in the listing for the identified state, then at Block 1830, the call is directed to the override telephone number. If not, then the call is directed to the main or default telephone number at Block 1840. Thus, embodiments of the present invention allow the IVR system to be configured to selectively direct telephone calls that are responsive to a selected AMBER alert to a selected authority who is responsible for the selected AMBER alert based upon a geographic area of the potential sighting, such as a state of the potential sighting. Embodiments of the present invention also allow the IVR system to be configured to selectively direct telephone calls that are responsive to a selected AMBER alert to a default telephone number for a selected authority who is responsible for the selected AMBER alert, absent an override telephone number for the selected AMBER alert. The telephone call may be selectively directed to the override telephone number that is provided for the given state if the override number is present.

Figure 20:
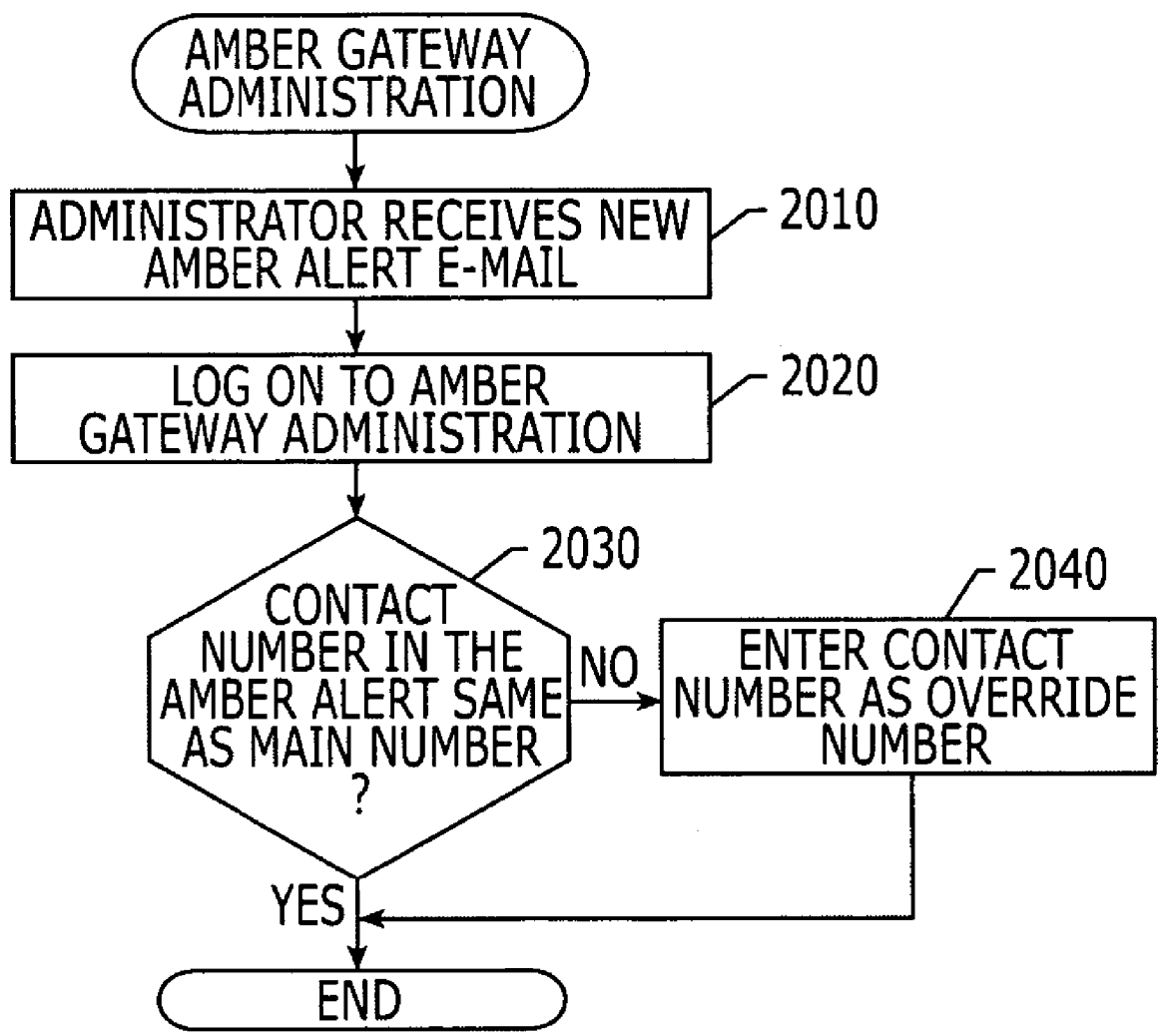
FIGS. 20–22 are flowcharts of operations that may be performed by AMBER gateways according to other embodiments of the present invention.

FIG. 20 is a flowchart of operations that may be performed for AMBER gateway administration according to some embodiments of the present invention. These operations may be performed, for example, by an administration system 1640 of FIG. 16. Initially, the administration system can populate the listing 1650 of FIG. 16 that is illustrated, for example, in FIG. 19, with the main or default numbers that are provided by each of the states. It will be understood that the listing of states in FIG. 19 is merely illustrative. Referring again to FIG. 20, at Block 2010, if an administrator such as a TSMC receives a new AMBER alert email, the administrator can log on to the AMBER gateway administration module 1640 at Block 2020. At Block 2030, a determination is made as to whether the contact number in the new AMBER alert email is the same as the main number. If so, no additional action need be taken. However, if the contact number in the new AMBER email alert is different from the main number, then the contact number is entered as the override number, at Block 2040. Thus, when the state overrides a general AMBER alert number for a specific AMBER alert, a caller may be directed to that override number.

Figure 21:
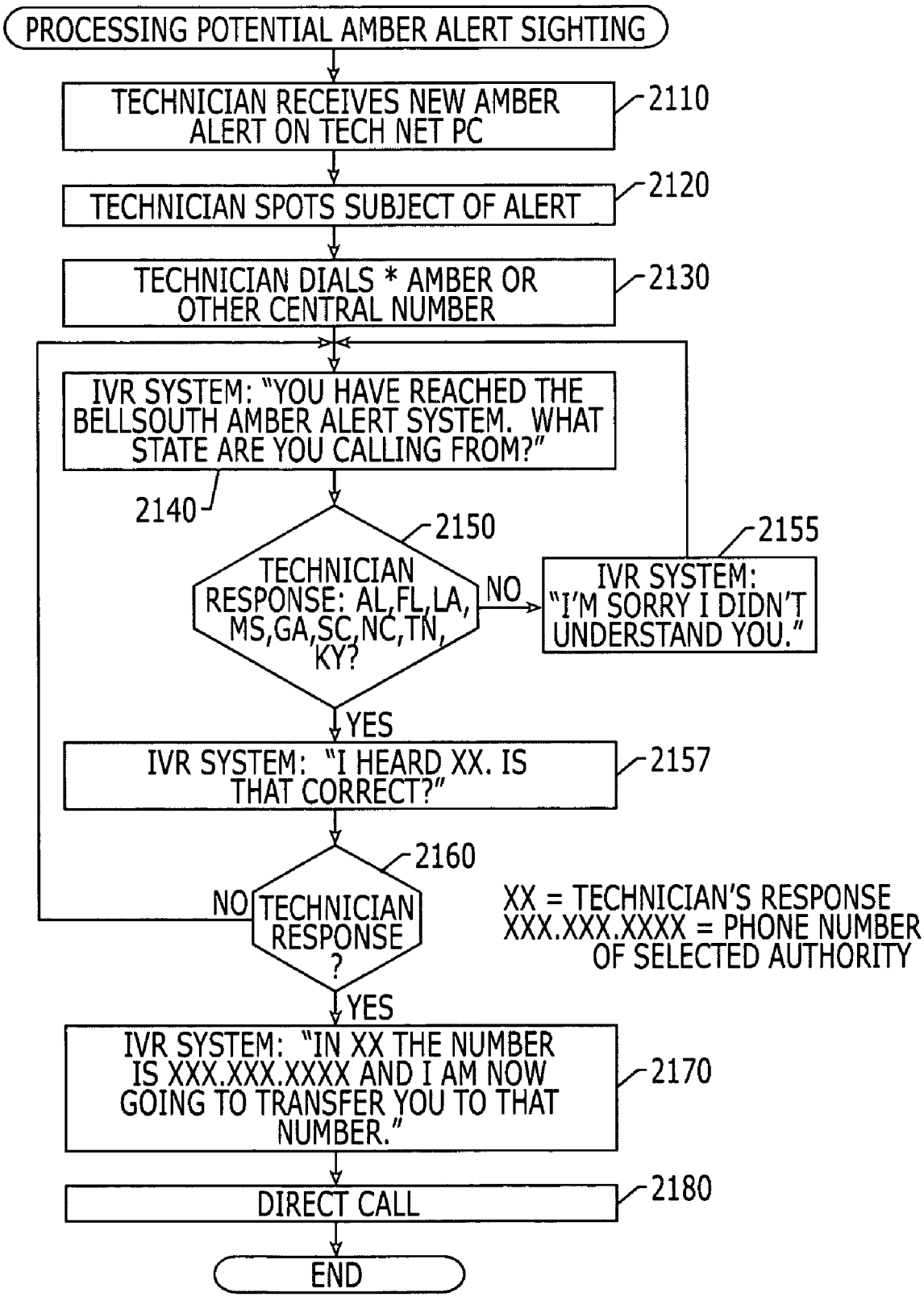

FIG. 21 is a flowchart of operations that may be performed to process potential AMBER alert sightings by a member of a mobile workforce, such as a technician, according to embodiments of the present invention. In particular, at Block 2110, a technician can receive a new AMBER alert on the Technet PC as was described, for example, in connection with FIGS. 4–15. At some point, at Block 2120, the technician spots the subject of the alert, also referred to as a potential sighting, as was described, for example, at Block 690 of FIGS. 6–8. At Block 2130, the technician dials *AMBER or another central number.

Interaction with the AMBER gateway then begins, as was described generally, for example, at Block 700 of FIGS. 6–7. In particular, at Block 2140, the IVR system provides an initial greeting and question that can state, for example, "You have reached the BellSouth AMBER alert system. What state are you calling from?". At Block 2150, the IVR system accepts a technician response of, for example, one of nine states for which the system is active. If the technician response is not one of these nine states, then at Block 2155, the IVR system can respond, for example, "I'm sorry. I didn't understand you.", and again ask the initial question at Block 2140. If the technician response is one of these nine states, then the IVR system verifies the state at Block 2157 by stating, for example, "I heard XX. Is that correct?", where XX is the state that was identified by the technician. At Block 2160, if the technician responds "no", then the operations of Block 2140 are performed again.

If, however, the technician confirms that this is the proper state, then the IVR system looks up the appropriate number in the listing, such as the listing of FIG. 19, and can provide a message to the user such as, "In XX, the number is XXX-XXX-XXXX, and I am now going to transfer you to that number.", where XXX-XXX-XXXX is the main or default number for the state. Thus, this message can confirm to the caller what state it is and also tell the caller what the number is, in case they are disconnected. At Block 2180, the call is then directed to the number that was identified. The AMBER gateway may then disconnect itself from the call, as was described, for example, in Block 1730 of FIG. 17, to free up that line.

Embodiments of the present invention were described in FIG. 21 with respect to processing AMBER alert sightings by a member of a mobile workforce, such as a technician. However, other embodiments of the present invention can be used by members of the general public to provide a central number which can be called by a member of the general public based on a potential AMBER sighting. Accordingly, as was described in connection with FIGS. 16–18, these embodiments can be provided apart from mobile workforce communication systems, methods and/or computer program products.

Figure 22:
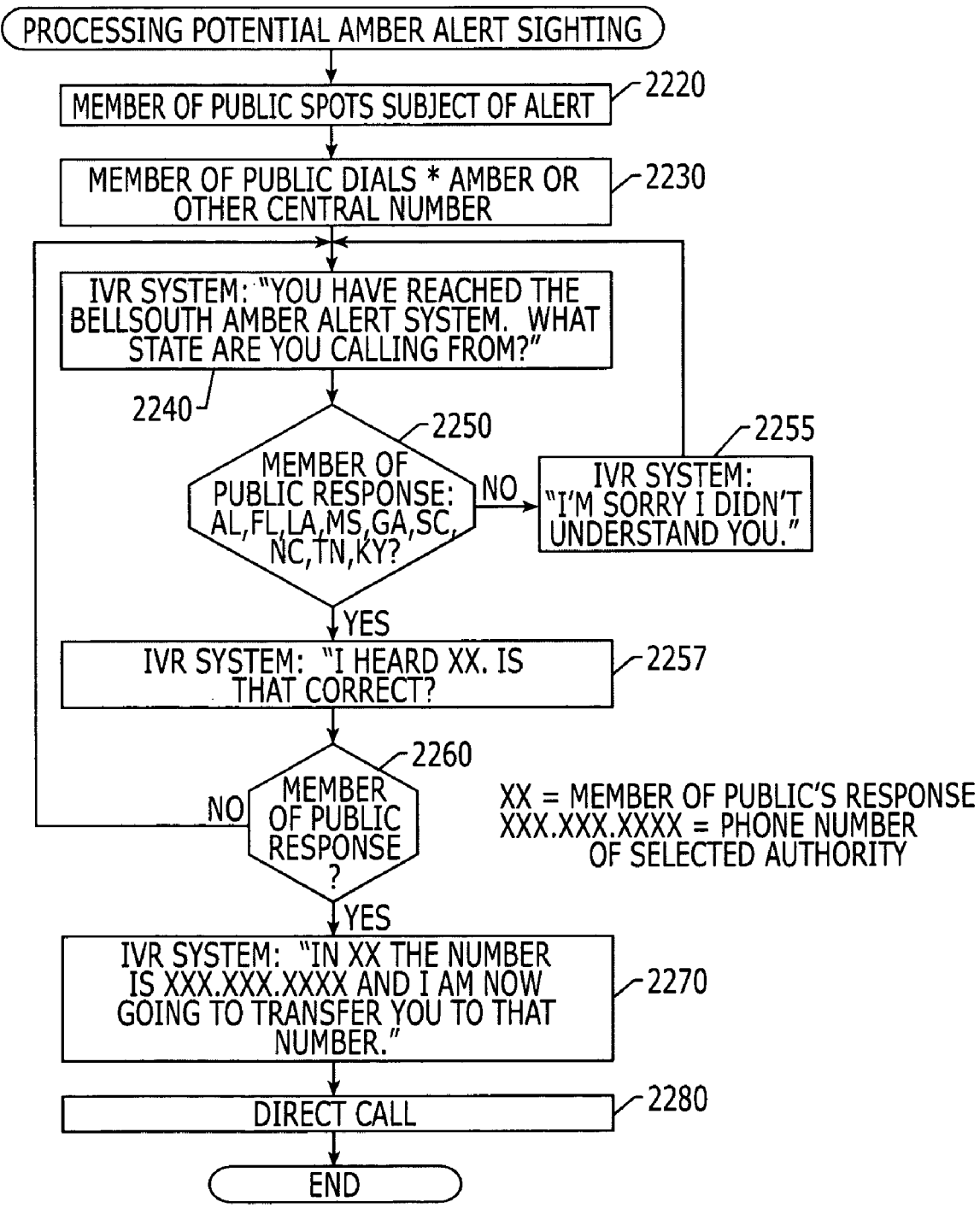

FIG. 22 is a flowchart of operations that may be performed to process potential AMBER alert sightings by a member of the public, according to embodiments of the present invention. The operations of Blocks 2220–2280 of FIG. 22 correspond to the operations 2120–2180 of FIG. 21, except that a "member of the public" replaces a "technician" in these operations. For brevity, these operations will not be described in detail again.

Accordingly, some embodiments of the present invention can provide a caller (a mobile workforce member and/or a member of the general public) with a toll-free number to call to report an AMBER alert-related sighting. A recording at the toll-free number allows the caller to select the state, and it can then forward the caller to the appropriate state agency or, in some embodiments, direct the caller to disconnect and dial 911. This may facilitate reporting a sighting for individuals who may be hesitant to dial 911. Accordingly, users may be provided with a single number to call for a potential sighting. Phone numbers that are received from each state are programmed into the system, so that when a user calls, for example, *AMBER or 1-888-31AMBER, they will be forwarded automatically via these numbers to the respective law enforcement agencies to report information in response to the AMBER alerts. In states that use the emergency number 911 as their reporting vehicle, users may be instructed to hang up and dial 911. Members of a mobile workforce may be provided a reminder decal inside their vehicles. The decal can say, "To report information in response to an AMBER alert, call *AMBER or 1-888-31AMBER".

In the drawings and specification, there have been disclosed typical embodiments of the invention and, although specific terms are employed, they are used in a generic and descriptive sense only and not for purposes of limitation, the scope of the invention being set forth in the following claims.

What is claimed is:

1. A mobile worlcforce communication system for a commercial business with a mobile sales and/or service workforce comprising:

a mobile workforce dispatch system that is configured to dispatch the mobile workforce of the commercial business to perform sales and/or service tasks for the commercial business;

a plurality of wireless terminals that are carried by the mobile workforce of the commercial business and are configured to communicate with the mobile workforce dispatch system to allow the mobile workforce to respond to dispatches to perform the sales and/or service tasks for the commercial business;

the mobile workforce dispatch system being further configured to accept an AMBER alert notification and to broadcast a mobile workforce AMBER alert message that comprises a description of an abductee and an identification of a location of an abduction, to the plurality of wireless terminals in response thereto so that the mobile workforce can be apprised of an AMBER alert while performing the sales and/or service tasks for the commercial business; and an AMBER gateway that is configured to receive a telephone call directly from a member of the mobile workforce of the commercial business without going through the mobile workforce dispatch system, in response to a potential sighting related to an AMBER alert and to direct the telephone call to an authority who is responsible for the AMBER alert.

2. A mobile workforce communication system according to claim 1 wherein the AMBER gateway is configured to receive a telephone call at a central telephone number from a member of the mobile workforce of the commercial business in response to a potential sighting related to an AMBER alert.

3. A mobile workforce corrununication system according to claim 2 wherein the central number is *AMBER for wireless telephone calls.

4. A mobile workforce communication system according to claim 1 wherein the AMBER gateway is configured to direct the telephone call to an authority who is responsible for the AMBER alert based upon a geographic area of the potential sighting.

5. A mobile workforce communication system according to claim 1 wherein the AMBER gateway is configured to direct the telephone call to an authority who is responsible for the AMBER alert by directing the telephone call to an overide telephone number for the AMBER alert.

6. A mobile workforce communication system according to claim 1 wherein the AMBER gateway is further configured to disconnect itself from the telephone call from the member of the mobile workforce of the commercial business after directing the telephone call to the authority who is responsible for the AMBER alert.

7. A mobile workforce communication system according to claim 1 wherein the AMBER gateway comprises an interactive voice response system that is configured to receive the telephone call from the member of the mobile workforce of the commercial business in response to the potential sighting related to the AMBER alert and to direct the telephone call to the authority who is responsible for the AMBER alert.

8. A mobile workforce communication system according to claim 1 wherein the mobile workforce AMBER alert message comprises the entire AMBER alert notification.

9. A mobile workforce communication system according to claim 1 wherein the mobile workforce dispatch system is configured to accept an AMBER alert notification that relates to a governmental jurisdiction and is further configured to broadcast a mobile workforce AMBER alert message only to selected ones of the plurality of wireless terminals that are located in the governmental jurisdiction.

10. A mobile workforce system for a commercial business having a mobile sales and/or service workforce comprising:

a mobile workforce communication system;

a plurality of wireless terminals that are carried by the mobile workforce of the commercial business and are configured to communicate with the mobile workforce communication system, to allow the mobile workforce to perform sales and/or service tasks for the commercial business;

the mobile workforce communication system being further configured to accept an AMBER alert notification and to broadcast a mobile workforce AMBER alert message that comprises a description of an abductee and an identification of a location of an abduction, to the plurality of wireless terminals in response thereto so that the mobile workforce of the commercial business can be apprised of an AMBER alert while performing the sales and/or service tasks for the commercial business; and an AMBER gateway that is configured to receive a telephone call directly from a member of the mobile workforce of the commercial business without going through the mobile workforce communication system in response to a potential sighting related to an AMBER alert and to direct the telephone call to an authority who is responsible for the AMBER alert.

11. A mobile workforce system according to claim 10 wherein the AMBER gateway is configured to receive a telephone call at a central telephone number from a member of the mobile workforce of the commercial business in response to a potential sighting related to an AMBER alert.

12. A mobile workforce system according to claim 11 wherein the central number is *AMBER for wireless telephone calls.

13. A mobile worlcforce system according to claim 10 wherein the AMBER gateway is configured to direct the telephone call to an authority who is responsible for the AMBER alert based upon a geographic area of the potential sighting.

14. A mobile workforce system according to claim 10 wherein the AMBER gateway is configured to direct the telephone call to an authority who is responsible for the AMBER alert by directing the telephone call to an override telephone number for the AMBER alert.

15. A mobile workforce communication system according to claim 10 wherein the AMBER gateway is further configured to disconnect itself from the telephone call from the member of the mobile workforce of the commercial business after directing the telephone call to the authority who is responsible for the AMBER alert.

16. A mobile workforce conunuunication system according to claim 10 wherein the AMBER gateway comprises an interactive voice response system that is configured to receive the telephone call from the member of the mobile workforce of the commercial business in response to the potential sighting related to the AMBER alert and to direct the telephone call to the authority who is responsible for the AMBER alert.

* * * * *